(12) United States Patent
Sharma

(10) Patent No.: US 7,550,602 B1
(45) Date of Patent: Jun. 23, 2009

(54) SMALL MOLECULE COMPOSITIONS FOR SEXUAL DYSFUNCTION

(75) Inventor: Shubh D. Sharma, Cranbury, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 621 days.

(21) Appl. No.: 11/036,281

(22) Filed: Jan. 14, 2005

Related U.S. Application Data

(60) Provisional application No. 60/536,690, filed on Jan. 14, 2004.

(51) Int. Cl.
*A01N 43/52* (2006.01)
*C07D 235/02* (2006.01)

(52) U.S. Cl. .................................. 548/300.4; 514/393
(58) Field of Classification Search .............. 548/300.4; 514/398, 393
See application file for complete search history.

(56) References Cited

U.S. PATENT DOCUMENTS

| | | |
|---|---|---|
| 6,350,760 B1 | 2/2002 | Bakshi et al. |
| 6,376,509 B1 | 4/2002 | Bakshi et al. |
| 6,410,548 B2 | 6/2002 | Nargund et al. |
| 6,458,790 B2 | 10/2002 | Palucki et al. |
| 6,472,398 B1 | 10/2002 | Palucki et al. |
| 6,534,503 B1 | 3/2003 | Dines et al. |
| 6,579,968 B1 | 6/2003 | Blood et al. |
| 2002/0004512 A1 | 1/2002 | Bakshi et al. |
| 2002/0137664 A1 | 9/2002 | Bakshi et al. |
| 2002/0143141 A1 | 10/2002 | Chen et al. |
| 2003/0069169 A1 | 4/2003 | Macor et al. |
| 2003/0083228 A1 | 5/2003 | Carpino et al. |
| 2004/0192676 A1 | 9/2004 | Chen |
| 2004/0254198 A1 | 12/2004 | Reynolds et al. |
| 2004/0266821 A1 | 12/2004 | Ujjainwalla et al. |
| 2005/0075344 A1 | 4/2005 | Backer et al. |
| 2005/0176728 A1 * | 8/2005 | Sharma et al. .......... 514/253.01 |
| 2005/0272718 A1 | 12/2005 | Ammenn et al. |

FOREIGN PATENT DOCUMENTS

| | | |
|---|---|---|
| WO | WO 02/18437 | 3/2002 |
| WO | WO 02/064091 | 8/2002 |
| WO | WO 03/006620 | 1/2003 |

OTHER PUBLICATIONS

Van der Ploeg, et al. A role for the melanocortin 4 receptor in sexual function. *Proc Natl Acad Sci USA* 99:11381-6 (2002).
Vergoni, et al. Chronic melanocortin 4 receptor blockage causes obesity without influencing sexual behavior in male rats. *J Endocrino*, 166:419-26 (2000).
*Synthetic Peptides: A User's Guide*, GA Grant, editor, W.H. Freeman & Co., New York, 1992, the teachings of which are incorporated herein by reference, including the text and table set forth at pp. 11 through 24.
Hruby VJ, Al-obeidi F and Kazmierski W: *Biochem J* 268:249-262, 1990.
Toniolo C: *Int J Peptide Protein Res* 35:287-300, 1990.
M.E. Hadley et al., Discovery and development of the novel melanogenic drugs, in *Integration of Pharmaceutical Discovery and Development: Case Studies*, edited by Borschart et al., Plenum Press, New York (1998).
R.T. Dorr et al., Evaluation of Melanotan-II, A Superpotent Cyclic Melanotropic Peptide in a Pilot Phase-I Clinical Study. *Life Sci.* 58:1777-1784 (1996).
R.A.H. Adan, Identification of Antagonists for Melanocortin MC3, MC4, and MC5 Receptors. *Eur. J. Pharmacol.*, 269:331-337 (1994).

* cited by examiner

*Primary Examiner*—James O Wilson
*Assistant Examiner*—Ebenezer Sackey
(74) *Attorney, Agent, or Firm*—Stephen A. Slusher

(57) ABSTRACT

Compounds of the general formula:

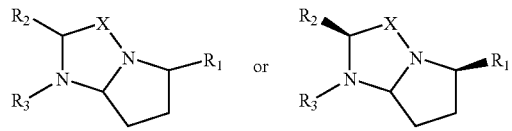

or a pharmaceutically acceptable salt thereof, wherein $R_1$, $R_2$, $R_3$, and X are as defined. Further provided are methods for treatment of sexual dysfunction, including erectile dysfunction and female sexual dysfunction, and combination drugs and method of use thereof, including a compound of the invention and one or more second sexual dysfunction pharmaceutical agents.

9 Claims, No Drawings

SMALL MOLECULE COMPOSITIONS FOR SEXUAL DYSFUNCTION

CROSS-REFERENCE TO RELATED APPLICATIONS

This application claims the benefit of the filing of U.S. Provisional Patent Application Ser. No. 60/536,690, entitled "Small Molecule Compositions for Sexual Dysfunction", filed on Jan. 14, 2004, and the specification thereof is incorporated herein by reference.

The subject of this application is related to U.S. patent application Ser. No. 11/031,898, entitled "Peptide Compositions for Treatment of Sexual Dysfunction", filed on Jan. 7, 2005, and to U.S. patent application Ser. No. 11/036,273, entitled "Metallopeptide Compositions for Treatment of Sexual Dysfunction", filed concurrently herewith, and the specification thereof of each is incorporated herein by reference.

BACKGROUND OF THE INVENTION

1. Field of the Invention (Technical Field)

The present invention relates to small ring-core molecules characterized in that they may be employed for the treatment of sexual dysfunction in mammals, including both male erectile dysfunction and female sexual dysfunction in humans, without modulating feeding behavior in mammals and without being substantially specific for any melanocortin receptor, including not substantially inhibiting binding at MC4-R, and methods for the treatment of sexual dysfunction in mammals without modulation of feeding behavior or eliciting or causing other responses characteristic of MC4-R specific molecules.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, midbrain and brainstem, and melanocortin-5 receptors (MC5-R), expressed in a wide distribution of tissues.

Compounds specific for MC3-R or MC4-R, and particularly MC4-R, are believed to be useful in regulation of energy homeostasis, including use as agents for attenuating food intake and body weight gain, for use in treatment of anorexia, as a weight gain aid, for treatment of obesity, and other treatment of food intake and metabolism-related disorders and conditions. Compounds specific for MC3-R and/or MC4-R, and particularly MC4-R, affect sexual response, and can be used as agents for treatment of sexual dysfunction, including male erectile dysfunction.

Most scientific investigators ascribe the sexual activity of melanotropin ligands to MC4-R. For example, see Van der Ploeg L H, Martin W J, Howard A D, Nargund R P Austin C P, Guan X, Drisko J, Cashen D, Sebhat I, Patchett A A, Figueroa D J, DiLella A G, Connolly B M, Weinberg D H, Tan C P, Palyha O C, Pong S S, MacNeil T, Rosenblum C, Vongs A, Tang R, Yu H, Sailer A W, Fong T M, Huang C, Tota M R, Chang R S, Stearns R, Tamvakopoulos C, Christ G, Drazen D L, Spar B D, Nelson R J, MacIntyre D E. A role for the melanocortin 4 receptor in sexual function. *Proc Natl Acad Sci USA* 99:11381-6 (2002). Evidence in favor of this hypothesis comes from the fact that a sexual response elicited by an MC4-R agonist can be blocked by an MC4-R antagonist. However, a few reports also suggest that MC4-R receptors may not be involved in eliciting sexual function response (Vergoni A V, Bertolini A, Guidetti G, Karefilakis V, Filaferro M, Wikberg J E, Schioth H B. Chronic melanocortin 4 receptor blockage causes obesity without influencing sexual behavior in male rats. *J Endocrino*, 166:419-26 (2000)).

Because of the myriad biological effects of compounds specific for melanocortin receptors, there is a need for compounds and methods, including methods of selection of compounds, to differentiate the effects. More specifically, there is a need for compounds that effect a sexual response, by the same or similar regulatory pathways as those implicated in MC4-R-specific compounds, without eliciting other biological effects related to MC4-R, including without limitation energy homeostasis or feeding behaviors. For most pharmaceutical applications it is desirably to have a compound that is specific for a single biological effect, such as for example a compound that regulates and elicits a sexual response, and that is not substantially specific for MC4-R, is not an agonist or antagonist with respect to MC4-R, and that does not regulate energy homeostasis, such as by decreasing food intake and/or body weight or elicit or cause other responses characteristic of MC4-R specific molecules.

BRIEF SUMMARY OF THE INVENTION

Small molecules are provided based on a ring core structure, and including as pendent groups at least an aromatic or substituted aromatic group, preferably phenyl or substituted phenyl group, including but not limited to a Phe or substituted Phe side chain moiety, one or more $C_1$ to $C_6$ aliphatic linear or branched groups, wherein at least one $C_1$ to $C_6$ aliphatic linear or branched group does not contain a cationic center, and an aromatic ring moiety, but specifically excluding 6,6 bicyclic rings in which one or both rings thereof are aromatic, such as specifically excluding naphthalene, which small molecules induce a sexual response without substantially binding melanocortin receptors, and may be employed for treatment of sexual dysfunction, but which do not activate MC4-R and thus are not agonists or partial agonists at MC4-R, and further do not affect energy homeostasis, such as altering food intake and/or body weight, and do not elicit or cause other responses characteristic of MC4-R specific molecules.

The invention thus provides a method for regulating or modulating sexual response, including penile erection in males, without regulating or modulating energy homeostasis, including feeding behavior, by administration of a therapeutically effective amount of a compound of this invention.

In one embodiment, the invention provides a compound of the general formula I:

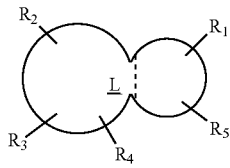

I wherein:

L is a conformationally restricted ring system consisting of a single ring or bicyclic non-aromatic carbocyclic ring system, a single ring or bicyclic aromatic carbocyclic ring system, a single ring or bicyclic non-aromatic heterocyclic ring system or a single ring or bicyclic aromatic heterocyclic ring system, with the single ring comprising from 5 to about 9 atoms, and the bicyclic ring system comprising from 5 to about 9 atoms in each ring, where the dashed line represents the common bond between shared atoms of the two rings when L is a bicyclic ring system;

$R_1$ is a bond or a linker unit comprising from one to six backbone atoms selected from the group consisting of carbon (C), oxygen (O) and nitrogen (N) and a ring group including at least one substituted or unsubstituted aromatic ring, including carbocyclic or heterocyclic aromatic rings, fused ring groups, bicylic ring groups, and bridged ring groups wherein at least one ring is an aromatic ring, but excluding 6,6-membered fused ring structures wherein at least one ring is an aromatic ring;

$R_2$ is hydrogen (H) or a $C_1$ to $C_6$ aliphatic linear or branched chain;

$R_3$ comprises a bond or a linker unit and at least one carbocyclic aromatic ring; and $R_4$ and $R_5$ independently are H or a $C_1$ to $C_6$ aliphatic linear or branched chain.

In compounds of formula I, or formula X as hereafter described, $R_1$, can be:

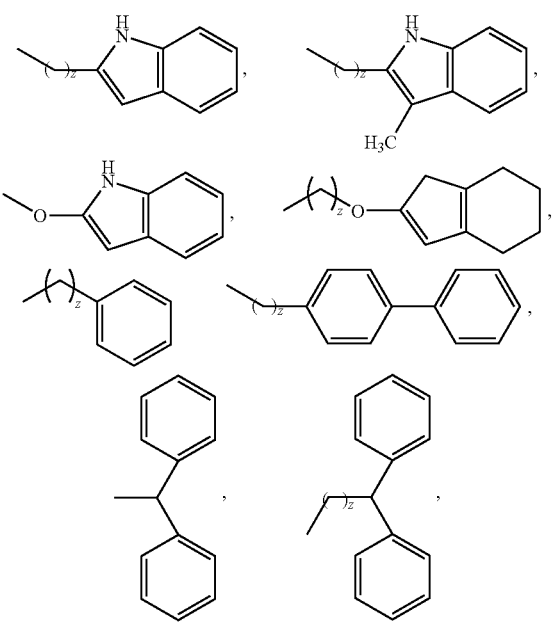

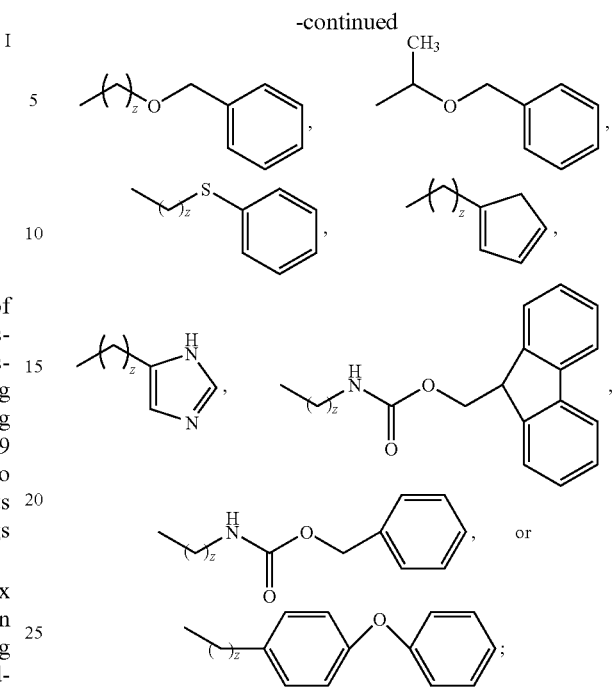

where z is from 1 to 5. The at least one aromatic ring of $R_1$, including those set forth above, can be functionalized with one or more halogen, alkyl or aryl groups.

In compounds of formula I, $R_2$ can be —$CH_3$, or —$(CH_2)_y$ $CH_3$, where y is from 1 to 5, or can be

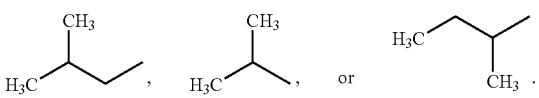

In compounds of formula I, or formula X as hereafter described, $R_3$ can include a natural or unnatural L- or D-amino acid with an aromatic group-containing side chain wherein the L ring system atom to which $R_3$ is bound is N. In a preferred embodiment $R_3$ includes a D-amino acid. $R_3$ can also further include an amine capping group. Thus in one embodiment $R_3$ is a D-isomer of Phe, Phe(4-F), Phe(4-Br), Phe(4-$CF_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-$CF_3$), Phe(3,4-diF), Phe(4-I), Phe(3,4-di-OMe), Phe(4-Me), Phe(4-OMe), Phe(4-NC), or Phe(4-$NO_2$). In another embodiment, $R_3$ is -$R_6$-$R_7$, where $R_6$ is a D-isomer of Phe, Phe(4-F), Phe(4-Br), Phe(4-$CF_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-$CF_3$), Phe(3,4-diF), Phe(4-I), Phe(3,4-di-OMe), Phe(4-Me), Phe(4-OMe), Phe(4-NC), or Phe(4-$NO_2$), and $R_7$ is -$R_8$, -$R_9$ or -$R_8$-$R_9$, where $R_8$ is between one and about three natural or unnatural L- or D-amino acid residues and $R_9$ is an amine capping group. $R_9$, the amine capping group, can be methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc.

In compounds of formula I, or formula X as hereafter described, the at least one carbocyclic aromatic ring of $R_3$ can include any of the following:

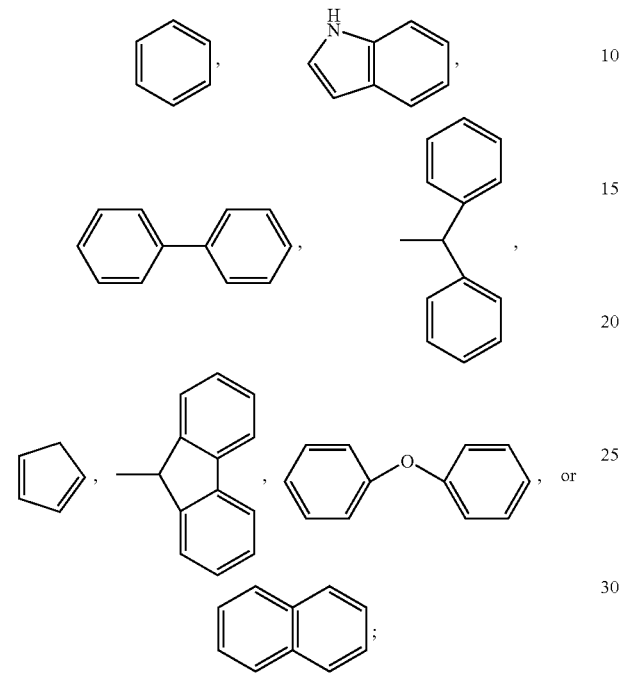

In the foregoing rings, at least one carbocyclic aromatic ring of $R_3$ can be functionalized with one or more halogen, alkyl or aryl groups.

In compounds of formula I, or formula X as hereafter described, preferably neither $R_4$ nor $R_5$ have a cationic center. In one embodiment, $R_4$ and $R_5$ can each independently be hydrogen, methyl, ethyl, propyl, butyl, pentyl, hexyl or a corresponding branched chain isomer.

In compounds of formula I, or formula X as hereafter described, the compound can be of any of the following formulas:

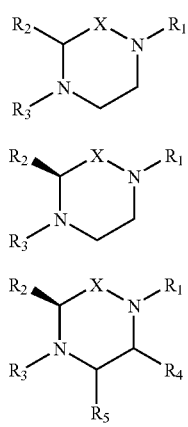

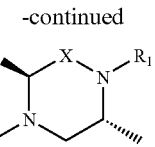

V

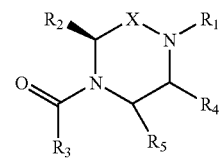

VI

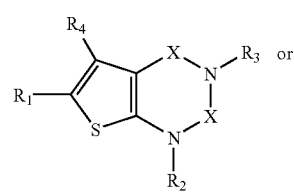

VII

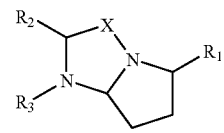

VIII

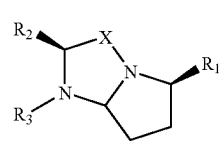

IX wherein $R_1$, $R_2$, $R_3$, $R_4$ and $R_5$ are as defined, X is in each instance $(CH_2)_n$, CH, NH, N, O, C=O, C=S, S, S=O or $SO_2$ and n is 0, 1, 2 or 3.

In another embodiment, the invention provides a compound of the general formula X:

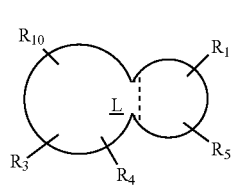

X wherein:

L is a conformationally restricted ring system consisting of a single ring or bicyclic non-aromatic carbocyclic ring system, a single ring or bicyclic aromatic carbocyclic ring system, a single ring or bicyclic non-aromatic heterocyclic ring system or a single ring or bicyclic aromatic heterocyclic ring system, with the single ring comprising from 5 to about 9 atoms, and the bicyclic ring system comprising from 5 to about 9 atoms in each ring, where the dashed line represents the common bond between shared atoms of the two rings when L is a bicyclic ring system;

$R_1$ is a bond or a linker unit comprising from one to six backbone atoms selected from the group consisting of C, O and N and a ring group including at least one substituted or unsubstituted aromatic ring, including carbocyclic or heterocyclic aromatic rings, fused ring groups, bicylic ring groups, and bridged ring groups wherein at least one ring is an aromatic ring, but excluding 6,6-membered fused ring structures wherein at least one ring is an aromatic ring;

$R_{10}$ is a $C_1$ to $C_6$ aliphatic linear or branched chain with a heteroatom unit without a cationic center, wherein at least one heteroatom is N;

$R_3$ comprises a bond or a linker unit and at least one carbocyclic aromatic ring; and $R_4$ and $R_5$ independently are H or a $C_1$ to $C_6$ aliphatic linear or branched chain.

In the compound of formula X, $R_{10}$ can be —$(CH_2)_y$NHCOCH$_3$, —$(CH_2)_y$NHCOOCH$_3$, —$(CH_2)_y$NHCONH$_2$, —$(CH_2)_y$NHCOH, —$(CH_2)_y$NHSO$_2$NH$_2$, —$(CH_2)_y$NHSO$_2$CH$_3$, or —$(CH_2)_y$CONH$_2$, where y is from 1 to 5.

Compounds of formula I or formula X can further be characterized in that the compound does not substantially inhibit the binding of α-MSH or an α-MSH analog to melanocortin receptors. Preferably the compound is therapeutically effective for treatment of sexual dysfunction.

In another embodiment, in the compounds of formula I or X, $R_3$ is alternatively one of the following aromatic groups:

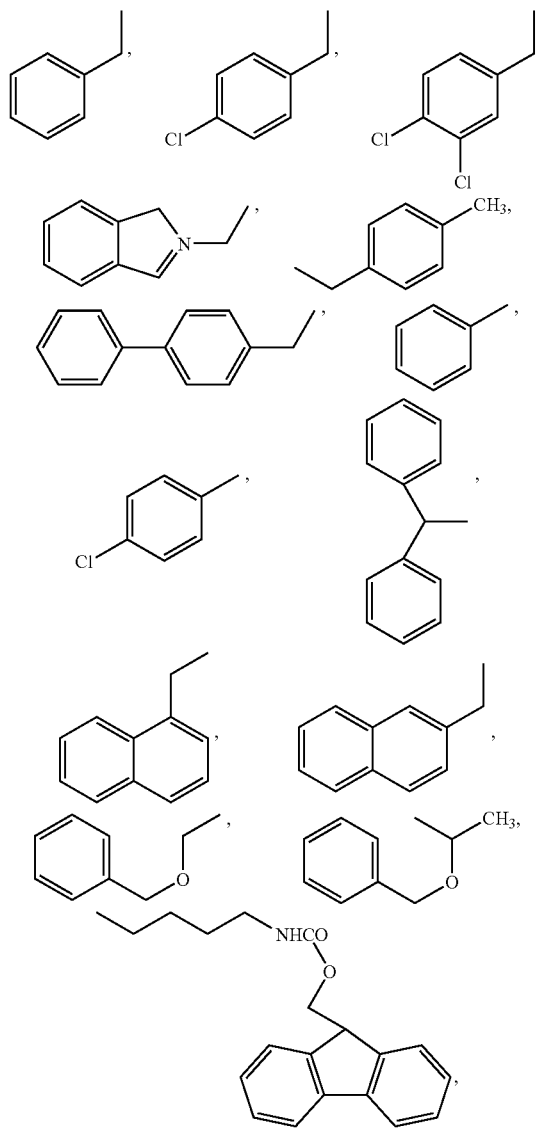

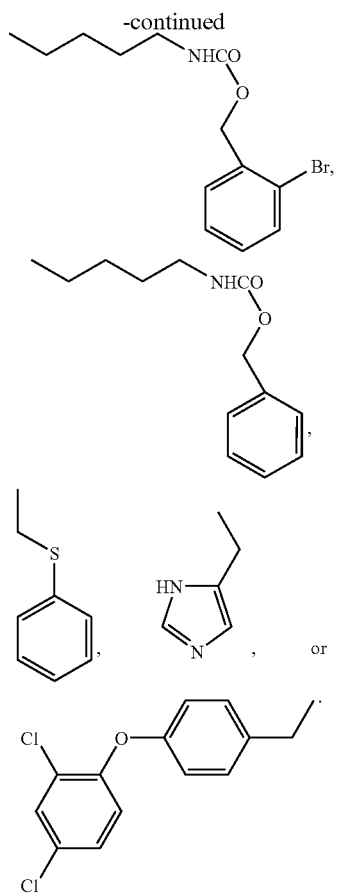

The invention further provides a pharmaceutical composition for treating sexual dysfunction in a mammal, including the compound of formula I through X as set forth above and a pharmaceutically acceptable carrier. The pharmaceutical composition can further include a second sexual dysfunction pharmaceutical agent.

The invention further provides a method of treating sexual dysfunction in a mammal, comprising administration of a therapeutically effective amount of a compound formula I through X as set forth above or a pharmaceutically acceptable salt thereof. The method can further include administration of a therapeutically effective amount of a second sexual dysfunction pharmaceutical agent, such as an MC4-R agonist or a PDE-5 inhibitor. In one embodiment of the method, the mammal is male and the sexual dysfunction is erectile dysfunction. In another embodiment, the mammal is female and the sexual dysfunction is female sexual dysfunction.

In general, a compound of any of the foregoing formulas, but which differs in that the group corresponding to $R_2$ has a cationic center, such as a $C_1$ to $C_6$ aliphatic linear or branched chain with a cationic center, such as for example a side chain moiety of Arg or Lys, may demonstrate efficacy for treatment of sexual dysfunction, such as by inducing a penile erection in a male mammal, but will also activate MC4-R and thus may be an agonist, partial agonist or antagonist at MC4-R, and thus will modulate energy homeostasis, such as in the case of an MC4-R agonist causing a decrease in food intake. Thus compounds where the group corresponding to $R_2$ is a $C_1$ to $C_6$ aliphatic linear or branched chain with a cationic center may be melanocortin-specific ligands, and such compounds may inhibit, or substantially inhibit, binding of $^{125}$I-NDP-α-MSH at MC3-R and/or MC4-R. Compounds where the group corresponding to $R_2$ is a $C_1$ to $C_6$ aliphatic linear or branched chain with a cationic center may induce a sexual response, but may also affect energy homeostasis, such as altering food intake and/or body weight, or elicit or cause other responses characteristic of MC4-R specific molecules. Based on data relating to these and other compounds, it is hypothesized that the absence of a cationic center at the $R_2$ position renders the compounds of this invention inactive, or substantially inactive, at melanocortin receptors, and specifically at MC3-R and/or MC4-R, but nonetheless such compounds may induce a sexual response, and may thus be employed for treatment of sexual dysfunction. Because of the inactivity or substantial inactivity of compounds without a cationic center at the $R_2$ position in any of a variety of melanocortin receptor-specific assays known in the art, it was not heretofore known that such compounds, notwithstanding such inactivity or substantial inactivity, elicit a sexual response, and thus may be employed for treatment of sexual dysfunction. This discovery thus provides compounds and methods for treatment of sexual dysfunction without otherwise causing biological or pharmacological effects associated with compounds specific for one or more melanocortin receptors, particularly compounds that are agonists or antagonists at MC3-R and/or MC4-R.

A primary object of the present invention is to provide a compound and method for initiating and/or maintaining a sexual response in a mammal, and for the treatment of sexual dysfunction in mammals, including both male erectile dysfunction and female sexual dysfunction in humans, without modulating feeding behavior.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

Definitions. Before proceeding further with the description of the invention, certain terms are defined as set forth herein.

The "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention includes any side chain of any amino acid, as the term "amino acid" is defined herein, including any derivative of an amino acid side chain moiety, as the term "derivative" is defined herein. Therefore, this includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, and saturated or unsaturated alkyl, aryl or aralkyl moieties.

The following abbreviations for amino acids, amino acid side chain moieties and derivatives and constituents thereof have the meanings giving, it being understood that any amino acid may be in either the L- or D-configuration:

| | |
|---|---|
| Abu | gamma-amino butyric acid |
| 2-Abz | 2-amino benzoic acid |
| 3-Abz | 3-amino benzoic acid |
| 4-Abz | 4-amino benzoic acid |
| Achc | 1-amino-cyclohexane-1-carboxylic acid |
| Acpc | 1-amino-cyclopropane-1-carboxylic acid |
| 12-Ado | 12-amino dodecanoic acid |
| Aib | alpha-aminoisobutyric acid |
| 1-Aic | 2-aminoindane-1-carboxylic acid |
| 2-Aic | 2-aminoindane-2-carboxylic acid |
| 6-Ahx | 6-amino hexanoic acid |
| Beta-Ala | beta-alanine |
| Amb | 4-(aminomethyl)-benzoic acid |
| Amc | 4-(aminomethyl)-cyclohexane carboxylic acid |
| 7'-amino-heptanoyl | $NH_2$—$(CH_2)_6CO$— |
| 8-Aoc | 8-amino octanoic acid |
| Arg(Tos) | $N^G$-para-tosyl-arginine |
| Asp(anilino) | beta-anilino-aspartic acid |
| Asp(3-Cl-anilino) | beta-(3-chloro-anilino)-aspartic acid |
| Asp(3,5-diCl-anilino) | beta-(3,5-dichloro anilino)-aspartic acid |
| Atc | 2-aminotetralin-2-carboxylic acid |
| 11-Aun | 11-amino undecanoic acid |
| AVA | 5-amino valeric acid |
| Beta-hHyp(Bzl) | beta-(O-benzyl)-homohydroxyproline |
| Beta-hSer(Bzl) | beta-(O-benzyl)-homoserine |
| Bip | biphenylalanine |
| Bzl | benzyl |
| Bz | benzoyl |
| Cha | cyclohexylalanine |
| Chg | cyclohexylglycine |
| Cmpi | 4-caboxymethyl-piperazine |
| Cys(Bzl) | S-benzyl-cysteine |
| Dip | 3,3-diphenylalanine |
| Disc | 1,3-dihydro-2H-isoindolecarboxylic acid |
| Dpr(beta-Ala) | $N^{beta}$-(3-aminopropionyl)-alpha,beta-diaminopropionic acid |
| Et | ethyl |
| GAA | epsilon-guanidino acetic acid |
| GBzA | 4-guanidino benzoic acid |
| B-Gpa | 3-guanidino propionic acid |
| GVA(Cl) | beta-chloro-epsilon-guanidino valeric acid |
| Heptanoyl | $CH_3$—$(CH_2)_5CO$— |
| hPhe | homophenylalanine |
| hSer | homoserine |
| Hyp | hydroxy praline |
| hHyp | homo hydroxy praline |
| Hyp(Bzl) | O-benzyl-hydroxyproline |

| | -continued |
|---|---|
| Hyp(2-naphthly) | O-2' naphthyl-hydroxyproline |
| Hyp(Phenyl) | O-phenyl-hydroxyproline |
| Idc | indoline-2-carboxylic acid |
| Igl | indanylglycine |
| Inp | isonipecotic acid |
| Lys(Z) | N-epsilon-benzyloxycarbonyl-lysine |
| Me | methyl |
| Nal 1 | 3-(1-naphthyl)alanine |
| Nal 2 | 3-(2-naphthyl)alanine |
| (N-Bzl)Nal 2 | N-benzyl-3-(2-naphthyl) alanine |
| 2-Naphthylacetyl | 2-naphthyl-$CH_2CO$— |
| (Nlys)Gly | N-(4-aminobutyl)-glycine |
| (N-PhEt)Nal 2 | N(2-phenylethyl)-3-(2-naphthyl) alanine |
| OcHx | cyclohexyl ester |
| Phg | phenylglycine |
| Phe(4-F) | para-fluoro-phenylalanine |
| Phe(4-Br) | 4-bromo-phenylalanine |
| Phe(4-$CF_3$) | 4-trifluoromethyl-phenylalanine |
| Phe(4-Cl) | 4-chloro-phenylalanine |
| Phe(3-Cl) | 3-chloro-phenylalanine |
| Phe(2-Cl) | 2-chloro-phenylalanine |
| Phe(2,4-diCl) | 2,4,-dichloro-phenylalanine |
| Phe(2,4-diF) | 2,4-difluoro-phenylalanine |
| Phe(3,4-diCl) | 3,4,-dichloro-phenylalanine |
| Phe(5-Cl) | 5-chloro-phenylalanine |
| Phe(2-Cl,4-Me) | 2-chloro-4-methyl-phenylalanine |
| Phe(2-Me,4-Cl) | 4-chloro-2-methyl-phenylalanine |
| Phe(2-F,4-Cl) | 4-chloro-2-fluoro-phenylalanine |
| Phe(2,4-diMe) | 2,4-dimethyl-phenylalanine |
| Phe(2-Cl,4-$CF_3$) | 2-chloro-4-trifluoromethyl-phenylalanine |
| Phe(3,4-diF) | 3,4,-difluoro-phenylalanine |
| Phe(4-I) | 4-iodo-phenylalanine |
| Phe(3,4-di-OMe) | 3,4,-dimethoxy-phenylalanine |
| Phe(4-Me) | 4-methyl-phenylalanine |
| Phe(4-OMe) | 4-methoxy-phenylalanine |
| Phe(4-NC) | 4-cyano-phenylalanine |
| Phe(4-$NO_2$) | 4-nitro-phenylalanine |
| Pip | pipecolic acid |
| Pr | propyl |
| Pr-i | isopropyl |
| 4-phenylPro | 4-phenyl-pyrrolidin-2-carboxylic acid |
| 5-phenylPro | 5-phenyl-pyrrolidin-2-carboxylic acid |
| 3-Pya | 3-pyridylalanine |
| Pyr | pyroglutamic acid |
| Qal(2') | beta-(2-quinolyl)-alanine |
| Sal | 3-styrylalanine |
| Sar | sarcosine |
| Ser(Bzl) | O-benzyl-serine |
| Ser(2-Naphthyl) | O-2-Naphthyl-serine |
| Ser(Phenyl) | O-2-Phenyl-serine |
| Ser(4-Cl-Phenyl) | O-4-Cl-Phenyl-serine |
| Ser(2-Cl-Phenyl) | O-2-Cl-Phenyl-serine |
| Ser(p-Cl-Bzl) | O-4-Cl-Benzyl-serine |
| Thr(Bzl) | O-Benzyl-threonine |
| Thr(2-Naphthyl) | O-(2-naphthyl)-threonine |
| Thr(Phenyl) | O-phenyl-threonine |
| Thr(4-Cl-Phenyl) | O-(4-Cl-phenyl)-threonine |
| Thr(2-Cl-Phenyl) | O-(2-Cl-phenyl)-threonine |
| Beta-homoThr(Bzl) | O-Benzyl-bate-homothreonine |
| Tic | 1,2,3,4-tetrahydroisoquinoline-3-carboxylic acid |
| Tiq | 1,2,3,4-tetrahydroisoquinoline-1-carboxylic acid |
| Tle | tert-butylalanine |
| Tpi | 1,2,3,4-tetrahydronorharman-3-carboxylic acid |
| Tyr(Bzl) | O-benzyl-tyrosine |
| Tyr(2,6-DiCl-Bzl) | O-(2,6 dichloro)benzyl-tyrosine |

Conventional amino acid residues have their conventional meaning as given in Chapter 2400 of the *Manual of Patent Examining Procedure*, 8th Ed. Thus, "Nle" is norleucine, "Asp" is aspartic acid, "His" is histidine, "D-Phe" is D-phenylalanine, "Arg" is arginine, "Trp" is tryptophan, "Lys" is lysine, "Gly" is glycine, "Pro" is praline, "Tyr" is tyrosine, "Ser" is serine and so on.

The following amino acids, or side chains thereof, may be employed, in either the L- or D-configuration as appropriate, in certain embodiments of this invention:

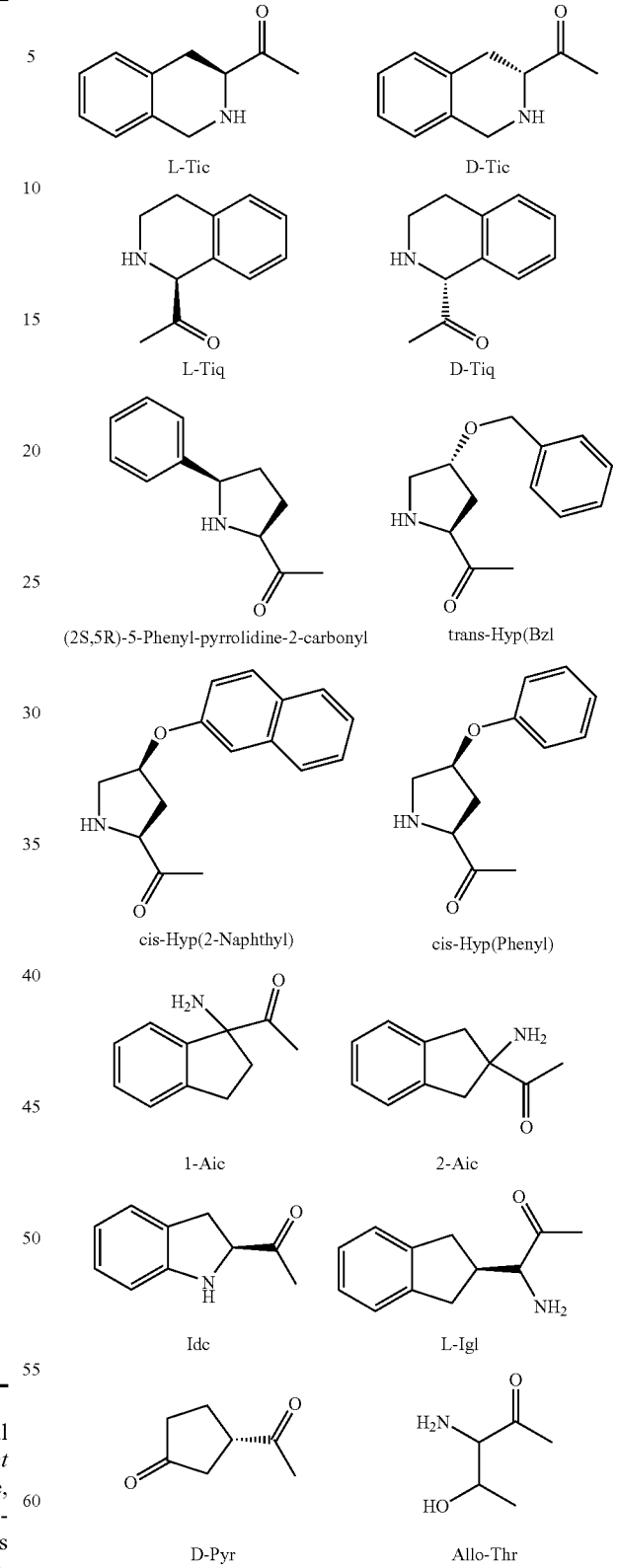

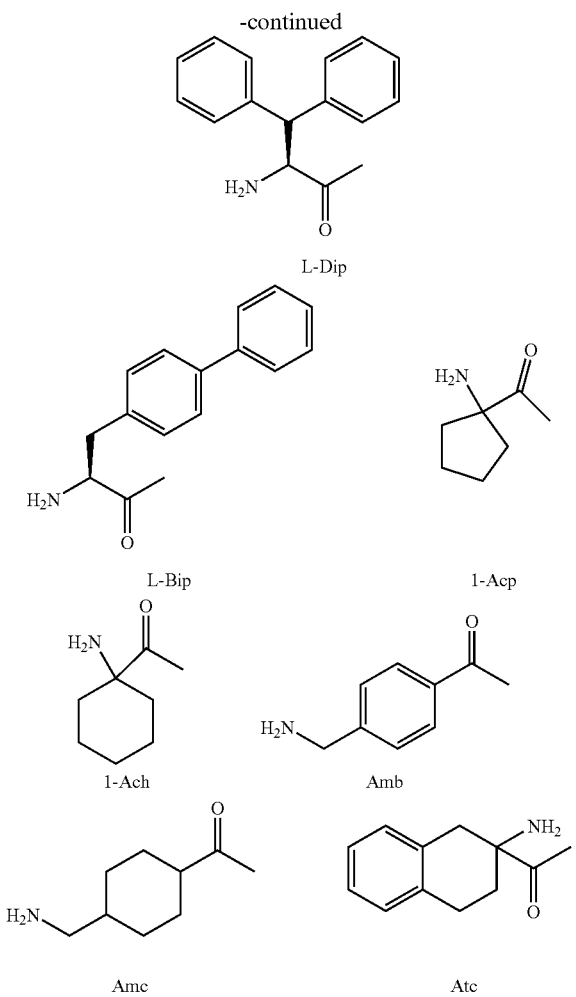

L-Dip

L-Bip

1-Acp

1-Ach

Amb

Amc

Atc

The term "homolog" includes, without limitation, (a) a D-amino acid residue or side chain substituted for an L-amino acid residue side chain, (b) a post-translationally modified residue or side chain substituted for the residue or side chain, (c) a non-protein or other modified amino acid residue or side chain based on another such residue or side chain, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxyl, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical—$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A group or aliphatic moiety is "acylated" when an alkyl or substituted alkyl group as defined above is bonded through one or more carbonyl {—(C=O)—} groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—$CO.NH_2$), such as methylamide, ethylamide, propylamide, and the like.

An "imide" includes compounds containing an imido group (—CO.NH.CO—).

An "amine" includes compounds that contain an amino group (—$NH_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

The term "halogen" is intended to include the halogen atoms fluorine, chlorine, bromine and iodine, and groups including one or more halogen atoms, such as —$CF_3$ and the like.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant an endogenous or drug substance or a compound that opposes the melanocortin receptor-associated responses normally induced by a melanocortin receptor agonist agent.

By "binding affinity" is meant the ability of a compound or drug to bind to its biological target.

An "amine capping group" includes any terminal group attached through a terminal amine, including but not limited to any omega amino derivative, acyl group or terminal aryl or aralkyl including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, as well as terminal groups such polyethylene glycol (PEG) with an average or formula molecular weight of between 100 and 10,000, optionally a PEG carboxylic acid derivative capable of forming a covalent bond with a terminal amine.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers, and optionally one or more pharmaceutically active ingredients and agents.

A variety of chemicals and compounds are employed in this invention, and the following abbreviations have the meanings given:

| | |
|---|---|
| AcOH | acetic acid |
| Boc | tertiary butyloxycarbonyl |
| Cbz | benzyloxycarbonyl |
| DCM | dichloromethane |
| DEAD | diethyl azodicarboxylate |
| DIAD | diisopropyl azodicarboxylate |
| DIC | 1,3-diisopropylcarbodiimide |
| EtOAc | ethyl acetate |
| Fmoc | 9-fluorenylmethoxycarbonyl |
| HEPES | 4-(2-hydroxyethyl)1-piperazineethanesulfonic acid |
| HOAt | 1-hydroxy-7-azabenzotriazole |
| IBCF | isobutyl chloroformate |
| LAH | lithium aluminum hydride |
| NMM | N-methyl-morpholine |
| Prt | A protecting group, such as Boc, Cbz or Fmoc |
| TBTU | 2-(1H-Benzotriazole-1-yl)-1,1,3,3-tetramethyluronium tetrafluoroborate |
| TEA | triethylamine |
| TFA | trifluoroacetic acid |
| THF | tetrahydrofuran |
| TPP | triphenylphosphine |

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

The compounds disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Combination Therapy. It is also possible and contemplated to use the compounds of this invention in combination with other drugs or agents. These other drugs and agents may include melanocortin receptor-specific agents that induce erectile activity, including specifically MC3-R and MC4-R agonists, phosphodiesterase-5 inhibitors, testosterone, prostaglandin and the like. In a preferred embodiment of the invention, compounds of the invention are used in combination with a therapeutically effective amount of a cyclic-GMP-specific phosphodiesterase inhibitor or an alpha-adrenergic receptor antagonist. Similarly, the compounds of this invention may be used in combination with any known mechanical aids or devices.

The present invention thus provides methods of treating sexual dysfunction, the methods comprising the step of administering to the patient having or at risk of having sexual dysfunction a therapeutically effective amount of a compound of this invention in combination with a therapeutically effective amount of a second sexual dysfunction pharmaceutical agent. The compound of this invention may be administered simultaneously with, prior to or subsequent to administration with a therapeutically effective amount of a second sexual dysfunction pharmaceutical agent. Preferably the compound of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the compound of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the compound of this invention when desired or needed by the patient.

The present invention thus provides methods of treating sexual dysfunction, the methods comprising the step of administering to a patient having or at risk of having sexual dysfunction a therapeutically effective amount of a compound of this invention in combination with a compound that is a melanocortin receptor agonist.

The present invention further also provides methods of treating sexual dysfunction, the methods comprising the step of administering to a patient having or at risk of having sexual dysfunction a therapeutically effective amount of a compound of this invention in combination with a compound that is a melanocortin receptor agonist and in combination with another compound that is useful in the treatment of sexual dysfunction.

In a preferred embodiment of combination therapy the sexual dysfunction is female sexual dysfunction.

In an especially preferred embodiment of combination therapy the sexual dysfunction is erectile dysfunction.

In a preferred embodiment of the foregoing methods, the melanocortin receptor agonist is an agonist of MC3-R or MC4-R, and preferably MC4-R. The agonist may be a nonselective MC3-R and MC4-R agonist.

The present invention also provides pharmaceutical compositions that comprise 1) a compound of this invention and 2) a compound that is a melanocortin receptor agonist.

The present invention also provides pharmaceutical compositions that comprise 1) a compound of this invention; 2) a compound that is a melanocortin receptor agonist; and 3) a third compound useful for the treatment of sexual dysfunction.

The present invention also provides pharmaceutical compositions that comprise 1) a compound of this invention and 2) a second compound useful for the treatment of sexual dysfunction.

Representative agonists of the melanocortin receptor which are a second compound useful in combination therapy are disclosed in the following publications, which are incorporated here by reference in their entirety: M. E. Hadley et al., Discovery and development of the novel melanogenic drugs, in *Integration of Pharmaceutical Discovery and Development: Case Studies*, edited by Borschart et al., Plenum Press, New York (1998); R. T. Dorr et al., Evaluation of Melanotan-II, A Superpotent Cyclic Melanotropic Peptide in a Pilot Phase-I Clinical Study. *Life Sci.* 58:1777-1784 (1996); and R. A. H. Adan, Identification of Antagonists for Melanocortin MC3, MC4, and MC5 Receptors. *Eur. J. Pharmacol.*, 269: 331-337 (1994).

In one embodiment of the composition above, the agonists are melanocyte-stimulating hormones (MSH) including α-, α-, and γ-MSH and/or adrenocorticotropic hormones (ACTH).

In another embodiment of the composition above, the melanocortin receptor agonist is Melanotan-II (MT-II). A preferred melanocortin receptor agonist includes any linear or cyclic melanocortin receptor-specific agonist peptide disclosed in International Application WO 03/006620 or a metallopeptide disclosed in International Application WO 02/064091. A particularly preferred melanocortin receptor agonist is Ac-Nle-cyclo(-Asp-His-D-Phe-Arg-Trp-Lys)-OH, as disclosed in U.S. Pat. No. 6,579,968. Alternatively, the agonist may be any agonist disclosed in any of the following patents or patent applications: U.S. Pat. No. 6,534,503, 6,472,398, 6,458,790, 6,410,548, 6,376,509, or 6,350,760; U.S. Published Application Nos. 2002/0137664, 2002/0004512, 2002/0143141, or US 2003/0069169; or International Application No. WO 02/18437. The agonist of the melanocortin receptor may preferably be selective for MC4-R.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; α-adrenergic antagonists; dopanergic ligands; androgens; selective androgen receptor modulators (SARMs); buproprion; vasoactive intestinal peptide (VIP); neutral endopeptidase inhibitors (NEP); neuropeptide Y receptor antagonists (NPY); and bombesin receptor-3 antagonists.

In an embodiment of the method and composition, the second sexual dysfunction pharmaceutical agent is testosterone.

In another embodiment of combination therapy, the second sexual dysfunction pharmaceutical agent is a type V phosphodiesterase inhibitor (PDE-5). For example, the PDE-5 inhibitor may be Viagra®, a brand of sildenafil, Levitra®, Clalis®, or may be 1-[[3-(6,7-dihydro-1-methyl-7-oxo-3-propyl-1-H-pyrazolo[4,3-d]pyrimidin-5-yl]-4-ethoxy-phenyl]sulfonyl)-4-methylpiperazine citrate salt, as disclosed in U.S. Published Application No. 2003/0083228.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolidin-1-yl-ethoxy)-phenyl]-5,6,7,8-tetrahydro-napth-thalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a compound of this invention may be used in combination with any known mechanical aids or devices.

The present invention also provides kits for the treatment of sexual dysfunction (including erectile dysfunction), the kits comprising: a first pharmaceutical composition including a compound of this invention; a second pharmaceutical composition comprising a second compound useful for the treatment of sexual dysfunction; and, a container for the first and second compositions.

Female Sexual Dysfunction. The compounds of this invention may be used to treat female sexual dysfunction as well as male sexual dysfunction. In general, the dosing schedules and doses for females are comparable to those for males.

The compounds of this invention, in that they are not specific for any heretofore known melanocortin receptor, may thereby define a new class of receptor, which receptor may be a protein receptor or may be an enzyme-associated receptor. The invention thus includes other compounds and structures that are functionally equivalent to the compounds of this invention. These other compounds are similarly characterized as effective in inducting erectile activity, preferably at very low doses, without being specific for any known melanocortin receptor.

Formulation and Utility

The methods, compounds and pharmaceutical compositions of this invention can be used for both medical applications and animal husbandry or veterinary applications Salt Form of Compounds. The compounds of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the compounds of this invention are prepared in a suitable solvent from the compound and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

Pharmaceutical Compositions. The invention provides a pharmaceutical composition that includes a compound of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The compositions of this invention may be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a compound of this invention over a period of time.

In general, the actual quantity of compounds of this invention administered to a patient will vary between fairly wide ranges depending on the mode of administration, the formulation used, and the response desired.

In practical use, the compounds of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or non-aqueous techniques. The amount of active compound in such therapeutically useful compositions is such that an effective dosage will be obtained. In another advantageous dosage unit form, sublingual constructs may be employed, such as sheets, wafers, tablets or the like. The compounds can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds may also be administered parenterally. Solutions or suspensions of compounds can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The compounds of this invention may be therapeutically applied by means of nasal administration. By "nasal administration" is meant any form of intranasal administration of any of the compounds of this invention. The compounds may be in an aqueous solution, such as a solution including saline, citrate or other common excipients or preservatives. The compounds may also be in a dry or powder formulation.

In an alternative embodiment, compounds of this invention may be administered directly into the lung. Intrapulmonary administration may be performed by means of a metered dose inhaler, a device allowing self-administration of a metered bolus of a compound of this invention when actuated by a patient during inspiration.

Routes of Administration. If it is administered by injection, the injection may be intravenous, subcutaneous, intramuscular, intraperitoneal or other means known in the art. The compounds of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the compounds of invention are introduced across an epidermal layer of cells may be employed. Administration means may thus include administration through mucous membranes, buccal administration, oral administration, dermal administration, inhalation administration, nasal administration, urethral administration, vaginal administration, and the like.

Therapeutically Effective Amount In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a compound or pharmaceutical composition of this invention that is sufficient to induce a sexual response, including inducing a penile erection in a male mammal.

In general, the compounds of this invention are highly active, with dose responses as low as 0.1 µg/kg, and optimal or peak dose responses typically between about 0.1 µg/kg and 25 µg/kg, depending on the specific compound and the route of administration. For example, the compound can be administered at 0.01, 0.05, 0.1, 0.5, 1, 5, 10, 50, 100, or 500 µg/kg body weight, depending on specific compound selected, the desired therapeutic response, the route of administration, the formulation and other factors known to those of skill in the art. Conventional dose response studies and other pharmacological means may be employed to determine the optimal dose for a desired effect with a given compound, given formulation and given route of administration.

Melanocortin Receptor Binding Assays. In a preferred embodiment, the compounds of the invention are characterized, in part, in that they do not inhibit, or do not substantially inhibit, the binding of α-MSH or an α-MSH analog to melanocortin receptors, and specifically MC1-R, MC3-R, MC4-R or MC5-R, such as by means of a competitive inhibition binding assay, where the concentration of the compound is at 1 µM. Thus the compound does not inhibit or substantially the binding of α-MSH or an α-MSH analog to MC4-R, where the concentration of the compound is at 1 µM. NDP-MSH is one example of an α-MSH analog. Similarly, in a preferred embodiment the compound does not inhibit or substantially inhibit the binding of α-MSH or an A-MSH analog to MC3-R, where the concentration of the compound is at 1 µM. Most preferably the compound is further not a melanocortin receptor agonist, and is specifically not a MC4-R agonist or a MC3-R agonist.

A competitive inhibition binding assay can be employed to determine inhibition of binding of α-MSH or an α-MSH analog, such as by using membranes prepared from hMC3-R, hMC4-R, hMC5-R, and B-16 mouse melanoma cells (containing MC1-R) using 0.4 nM $^{125}$I-NDP-MSH (0.2 nM for MC1-R) (New England Nuclear, Boston, Mass., USA) in 50 mM HEPES buffer containing 1 mM $MgCl_2$, 2 mM $CaCl_2$, and 5 mM KCl, at pH 7.2. The assay tube contains a chosen concentration of the compound of this invention, most preferably 1 µM, for determining inhibition of the binding of $^{125}$I-NDP-MSH to its receptor. Non-specific binding is measured by complete inhibition of binding of $^{125}$I-NDP-MSH in the assay in the presence of 1 µM α-MSH. Incubation is for 90 minutes at 37° C., after which the assay mixture is filtered and the membranes washed three times with ice cold buffer. The filter is dried and counted in a gamma counter for remaining radioactivity bound to the membranes. 100% specific binding is defined as the difference in radioactivity (cpm) bound to cell membranes in the absence and presence of 1 µM α-MSH. The cpm obtained in the presence of compounds of this invention is normalized with respect to 100% specific binding to determine the percent inhibition of $^{125}$I-NDP-MSH binding.

A compound does not "inhibit" α-MSH binding, determined by inhibition of binding of $^{125}$I-NDP-MSH, when the measured percent inhibition is less than about 10%, and preferably when no inhibition is detectable (the measured percent inhibition is 0% or less), where the concentration of the compound is at 1 µM. A compound does not "substantially inihibit" α-MSH binding when the measured percent inhibition is less than about 40%, where the concentration of the compound is at 1 µM.

Functional assays to determine agonist or antagonist status of a compound may be conducted by any means known in the art. In one method, a cAMP assay is performed. Human MC4-R cells are grown to confluence in 96 well plates (plating approximately 250,000 cells per well). Identical sets of cells in triplicate are treated with 0.2 mM isobutylmethylxanthine (IBMX) and the chosen concentration of the compound or alternatively the compound in the presence of 20 nM NDP-MSH. Cells similarly treated but with only 20 nM NDP-MSH serve as positive control. A buffer blank, as a negative control, is also included. Incubation is for one hour at 37° C. after which the cells are lysed by the addition of 50 μL of a cell lysis buffer. Total cAMP accumulated in 250 μL of this solution is quantitated using a commercially available low pH cAMP assay kit (Amersham BioSciences) by the procedure specified by the kit supplier. Any test subject showing cAMP accumulation in the same range as or higher than the positive control (buffer blank in the presence of α-MSH) is considered to be an agonist. A test subject showing accumulation in the same range as the negative control (buffer blank in the absence of α-MSH) is ineffective at the test concentration if the result is similar to the positive control where α-MSH is also present in the assay. A test subject showing accumulation in the same range as the negative control is considered to be an antagonist if there is inhibition in cAMP when α-MSH is present in the assay. Similar methods may be employed for MC3-R, using MC3-R cells. Compounds of this invention are, in one particularly preferred embodiment, ineffective at any concentration, and thus are neither an agonist nor an antagonist with respect to MC4-R.

In a particularly preferred embodiment, the compounds of the invention are effective for treatment of sexual dysfunction but do not cause a biologically response associated with activation or inhibition of a melanocortin receptor, such as at 1 μM concentration or lower, particularly MC3-R and/or MC4-R, and thus do not modulate feeding behavior in mammals or elicit or cause other responses characteristic of MC4-R specific molecules, including without limitation treatment of obesity or diabetes mellius such as associated with MC3-R or MC4-R specific agonists, or treatment of cachexia or wasting disease associated with cancer, AIDS, failure to thrive syndrome, and diseases associated with aging and senility such as associated with MC4-R specific antagonists.

The invention is further illustrated by the following non-limiting examples.

EXAMPLE 1

A competitive inhibition binding assay is conducted using membranes prepared from hMC3-R, hMC4-R, hMC5-R, and B-16 mouse melanoma cells (containing MC1-R) using 0.4 nM $^{125}$I-NDP-α-MSH (New England Nuclear, Boston, Mass., USA) in 50 mM HEPES buffer containing 1 mM $MgCl_2$, 2 mM $CaCl_2$, and 5 mM KCl, at pH 7.2. The assay tube also contains a chosen concentration of the test compound of this invention, preferably a concentration of 1 μM, for determining its efficacy in inhibiting the binding of $^{125}$I-NDP-α-MSH to its receptor. Non-specific binding is measured by complete inhibition of binding of $^{125}$I-NDP-α-MSH in the assay with the presence of 1 μM α-MSH.

Incubation is for 90 minutes at room temperature, after which the assay mixture was filtered and the membranes washed three times with ice cold buffer. The filter is dried and counted in a gamma counter for remaining radioactivity bound to the membranes. 100% specific binding is defined as the difference in radioactivity (cpm) bound to cell membranes in the absence and presence of 1 μM α-MSH. The cpm obtained in presence of test compounds are normalized with respect to 100% specific binding to determine the percent inhibition of $^{125}$I-NDP-α-MSH binding. Each assay is conducted in triplicate and the actual mean values are described.

EXAMPLE 2

Functional evaluation of compounds at melanocortin receptors is performed by measuring the accumulation of intracellular cAMP in HEK-293 cells expressing MC3-R, MC4-R or MC5-R, and in B-16 mouse melanoma cells (containing MC1-R). Cells, suspended in Earle's Balanced Salt Solution containing 10 mM HEPES, pH 7.5, 5 mM $MgCl_2$, 1 mM glutamine, 0.1% albumin and 0.6 mM 3-isobutyl-1-methyl-xanthine, a phosphodiesterase inhibitor, are plated in 96 well plates at a density of $0.5 \times 10^5$ cells per well. Cells are incubated with the test compounds, preferably at a concentration of 1 μM, in the presence or absence of α-MSH for 1 hour at 37° C. cAMP levels are measured by EIA (Amersham) in the cell lysates. Data analysis and $EC_{50}$ values are determined using nonlinear regression analysis with Prism Graph-Pad software.

EXAMPLE 3

The agonist/antagonist status with respect to MC4-R of certain compounds of the invention is determined. Antagonistic activity is determined by measuring the inhibition of α-MSH-induced cAMP levels following exposure to the compounds as in Example 2.

EXAMPLE 4

The ability of compounds to induce penile erection (PE) in male rats is evaluated with selected compounds. Male Sprague-Dawley rats weighing 200-250 g are kept on a 12 hour on/off light cycle with food and water ad libitum. All behavioral studies are performed between 10 a.m. and 5 p.m. Groups of 4-8 rats are treated with compounds at a variety of doses via intravenous (IV) or intracerebroventricular (ICV) routes. Immediately after treatment, rats are placed into individual polystyrene cages (27 cm long, 16 cm wide, and 25 cm high) for behavioral observation. Rats are observed for 30 minutes (for IV treated rats) or 120 minutes (for ICV treated rats) and the number of yawns, grooming bouts and PEs are recorded in 10-minute bins.

EXAMPLE 5

Change in food intake and body weight are evaluated for selected compounds. Male Sprague-Dawley rats weighing ~300 g at the beginning of the experiment are kept on a 12 hour on/off light cycle. Lights out is adjusted to 12:00 p.m. to allow for dosing just prior to the start of their dark period. Rats (8-12/group) were fed powdered chow and water ad libitum. For 1 week before treatment, 24-hour food intake and body weight change is recorded to assess a baseline for the group during vehicle treatment. The rats are dosed ICV with vehicle or selected compounds (1-3 nmol) or IV with vehicle or selected compounds (0.5-3 mg/kg). The changes in body weight and food intake for the 24 hour period after dosing are determined. The changes in body weight and food intake for the 48 hour period, and in some cases the 72 hour period, after dosing is also measured to determined reversal of changes in body weight and food intake effect back to baseline.

EXAMPLE 6

The following compound of formula VIII:

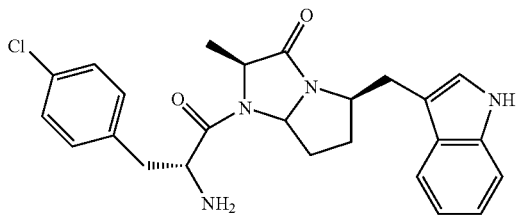

is synthesized by conventional methods. Briefly, in synthesis the following steps are employed, as set forth in Scheme 1:

To N-(tert-butoxycarbonyl)-L-tryprophan, N-methyl morpholine (1 equivalent) in dry DCM is added TBTU (1 equivalent). The mixture is stirred at room temperature for 30 minutes. A mixture of N,O-dimethylhydroxyamine hydrochloride (1.5 equivalent) and NMM (1.5 equivalent) in DCM is stirred for 30 minutes. These two mixtures are combined and stirred at room temperature for 18 hours. The organic solvent is evaporated and the residue is purified by flash chromatography to give N-(tert-butoxycarbonyl)-tryprophan, N,O-dimethyl-hydroxamide. The resulting N-(tert-butoxycarbonyl)-tryprophan, N,O-dimethyl-hydroxamide is dissolved in dry THF. The solution is cooled to 0° C. under nitrogen atmosphere. To this solution is added LAH (1 M in THF, 1.25 equivalent) slowly. The solution is stirred at this temperature for 30 minutes. The reaction is stopped by adding potassium hydrogensulfate (1.5 equivalent) in water. After stirring for 30 minutes, the solvent is removed and re-dissolved in ether. The organic phase is washed by 1 N hydrochloric acid, saturated sodium hydrogen carbonate and brine. The ether layer is dried over sodium sulfate. Solvent is removed to give an aldehyde derivative A, which is used for next step reaction without further purification.

Compounds A and N-methoxy-N-methyl-2-(triphenylphosphoranylidene)acetamide (2 equivalent) in methylene chloride are stirred for 16 hours. The solvent is evaporated and the residue is purified on a silica gel column to give a compound mainly with (E)-olefin. This compound is subsequently subjected to the treatment by hydrogen with catalytic amount of Pd on carbon (10%) in EtOAc for 10 hours. After filtration and evaporation of solvent compound B is obtained for the next step reaction without further purification.

Compound B is treated with 25% TFA in methylene chloride for one hour. The solvent is removed. The compound is neutralized by N-methylmorpholine, which is then added to a mixture of Z-Ala-OH, N-methyl morpholine (1 equivalent) and TBTU (1 equivalent) in dry DCM. The reaction is carried out for 16 hours at room temperature. Solvent is removed and the residue purified on silica gel column to give compound C.

Compound C is dissolved in dry THF. The solution is cooled to 0° C. under nitrogen atmosphere. To this solution is added LAH (1 M in THF, 1.25 equivalent) slowly. The solution is stirred at this temperature for 30 minutes. The reaction is stopped by adding potassium hydrogen sulfate (1.5 equivalent) in water. After stirring for 30 minutes, the solvent is removed and re-dissolved in ether. The organic phase is washed with 1 N hydrochloric acid, saturated sodium hydrogenc arbonate and brine. The ether layer is dried over sodium sulfate. Solvent is removed to give an aldehyde derivative, which is then used for next step reaction without further purification.

The aldehyde derivative is dissolved in DCM containing catalytic amounts of TFA. The solution is refluxed for 5 hours. After removing solvent, the residue is purified on column to give Cbz-protected compound D, which is dissolved in methanol in the presence of catalytic amount of palladium on carbon (10%). The mixture is stirred under hydrogen (1 atmosphere) overnight. After filtration and evaporation of solvent, the residue is dried under vacuum to give compound D.

Compound D is coupled with desired amino acids (2 equivalent) by use of HOAt (2 equivalent) and DIC (2 equivalent) in N,N-dimethylformamide solution overnight at room temperature. Flash chromatography (EtOAc/hexane=2) gives the product with protecting groups. The Fmoc protecting group is removed by treatment with 20% diethyl amine in EtOAc and the Boc protecting group is removed by treatment with 30% TFA in methylene chloride for 1 hour, as applicable to the compounds. The final pure compound E is obtained by purification on HPLC.

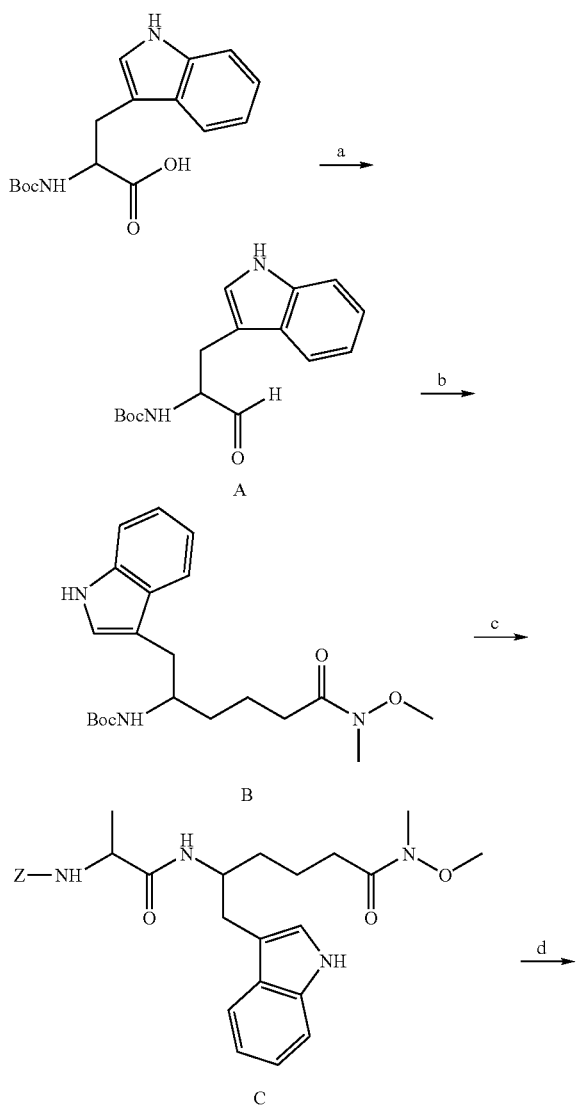

Scheme 1

-continued

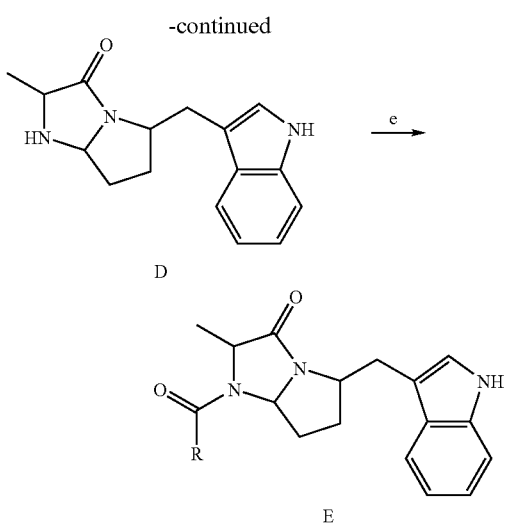

D

E

Reagents: (a) i) TBTU, NMM, MeNHOMe, DCM; ii) LAH, THF; (b) i) Ph₃P=CH₂CONMeOMe, DCM; ii) Pd/C, H₂, MeOH; (c) i) TFA/DCM; ii) Z-Ala-H, TBTU, NMM, DCM; (d) i) TFA (cat.), DCM, reflux; ii) Pd/C, H₂, MeOH; (e) i) RCOOH, HOAt, DIC; ii) TFA/DCM.

To make the compound of Example 6, compound D is coupled with Boc-D-Phe(4-Cl) as described and the Boc group is removed by treatment with 30% TFA in methylene chloride for 1 hour as described.

The compound is tested for competitive inhibition at melanocortin receptors, Ki (nM) at melanocortin receptors, functional status at melanocortin receptors, ability to induce penile erection and food intake and body weight change, as in Examples 1 to 5.

EXAMPLE 7

The following compound of formula VI wherein $R_2$ is H and $R_4$ and $R_5$ are each —CH₃:

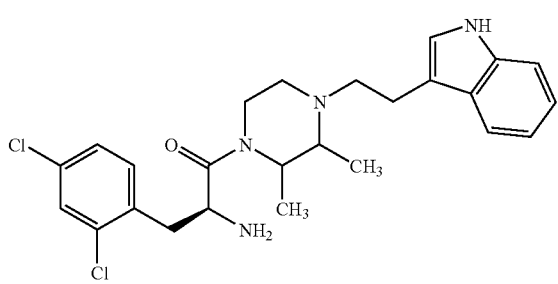

is synthesized by conventional methods. Briefly, in synthesis the following steps are employed, as set forth in Scheme 2:

To a solution of Indole-3-AcOH and HOAt (1 equivalent) in dry N,N-dimethylformamide is added 1-(3-dimethylaminopropyl)-3-ethylcarbodiimide hydrochloride (2 equivalent). After the mixture is stirred at room temperature for half an hour, 2-amino-3-butanol (2 equivalent) is added. The reaction is continued for 16 hours. The reaction mixture is poured into water and extracted by EtOAc twice. The organic layer is washed by 1 N hydrochloric acid twice, 1 N sodium hydroxide twice, brine and dried over sodium sulfate. After evaporating the solvent, the product is purified on silica gel column with 10% methanol on methylene chloride. To this compound (1 equivalent) and sodium borohydride (5 equivalent) in dioxane is added AcOH (5 equivalent) in dioxane slowly. After completion the mixture is refluxed for 2 hours, and the reaction is quenched by water. The product is extracted from ether by 1 N hydrochloric acid. The pH value of the aqueous solution is adjusted with potassium hydroxide to around 11 and the product is extracted by ether three times. The organic layer is dried over sodium sulfate and solvent is evaporated. The obtained compound A is used for next step reaction without further purification.

To compound B (1 equivalent), N-methyl morpholine (1 equivalent) in dry DCM, is added TBTU (1 equivalent). The mixture is stirred at room temperature for 30 minutes. A mixture of N,O-dimethylhydroxyamine hydrochloride (1.5 equivalent) and NMM (1.5 equivalent) in DCM is stirred for 30 minutes. These two mixtures are combined and stirred at room temperature for 18 hours. The organic solvent is evaporated, the residue loaded on a flash chromatography column and eluted with ethyl acetae/hexane (2/1) to give an N,O-dimethylhydroxyamide product. This product is dissolved in dry THF at 0° C. and LAH (1 M in THF, 1.2 equivalent) is added slowly. After 30 minutes the reaction is quenched by aqueous potassium hydrogen sulfate (1.2 equivalent). THF is removed and ether added. The solution is washed by 1 N HCl (2 times), aqueous sodium hydrogen carbonate, and subsequently brine, and dried over sodium sulfate. The solvent is removed under vacuum to give compound C. Compound C is used for next step reaction without further purification.

A mixture of compound C and compound A is stirred in the presence of activated 4 Å molecular sieves (1 gram) in dry THF (10% AcOH) for 1 hour. Sodium cyanoborohydride (1 equivalent, 1 M solution in THF) is added to this mixture. After 2 hours, solvent is evaporated and the desired product D is purified by silica gel column.

Compound D is treated with 20% diethylamine in EtOAc for 12 hours and the solvent evaporated to dryness. The residue and TPP (3 equivalent) is dissolved in dry THF. To this solution is added DIAD (3 equivalent) in THF slowly at 0° C. The reaction is continued for 16 hours at room temperature. The resulting product E is purified by silica gel column after evaporation of solvent.

Compound E is coupled with the desired amino acid(s) (2 equivalent) by use of HOAt (2 equivalent) and DIC (2 equivalent) in N,N-dimethylformamide solution overnight at room temperature. Flash chromatography (EtOAc/hexane=2) gives the product with protection groups. The Fmoc group is removed by treatment with 20% diethyl amine in EtOAc, or alternatively the Boc group is removed by treatment with 30% TFA in methylene chloride for 1 hour, as applicable to the compounds. The final pure compounds F are obtained by purification on HPLC.

Scheme 2

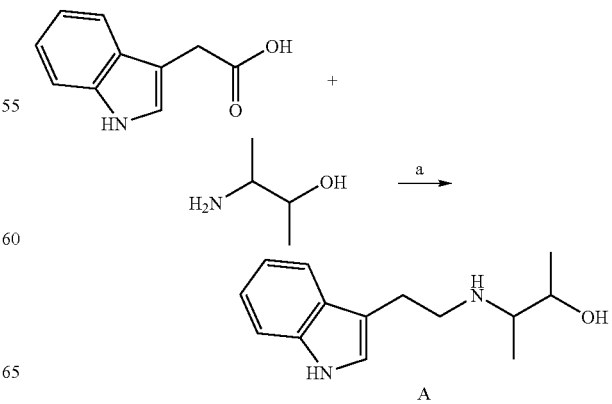

A

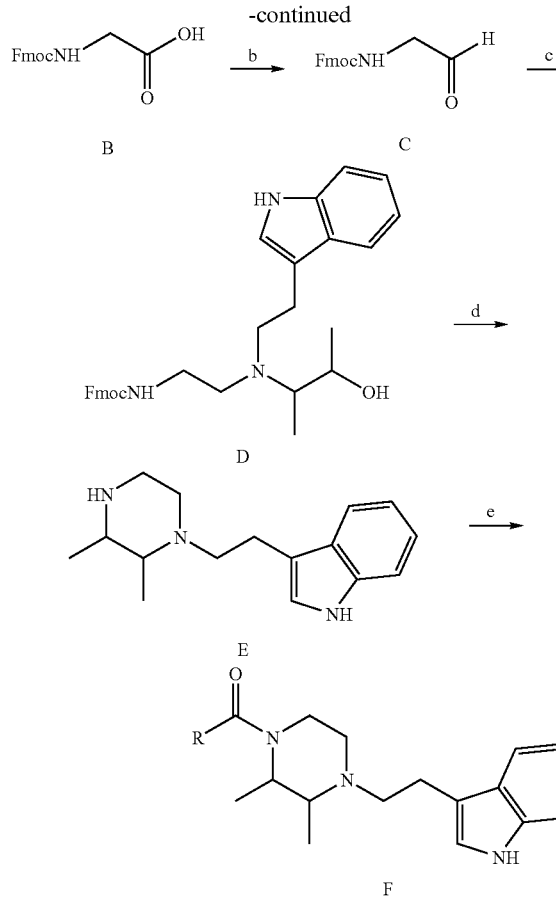

Reagents: (a) i) HOAt, EDC, DMF; ii) NaBH₄, HOAc, Dioxane, reflux. (b) i) NHMeOMe.HCl, TBTU, NMM; ii) LAH, THF; (c) 4A molecular sieves, A, NaBCNH₃, HOAc/THF. (d) i) 20% Et₂NH/EtOAc; ii) Ph₃P, DIAD, THF; (e) i) RCOOH, HOAt, DIC, DMF; ii) TFA/DCM To make the compound of Example 7, compound E is coupled with Boc-L-Phe(2,4-di-Cl) as described and the Boc group is removed by treatment with 30% TFA in methylene chloride for 1 hour as described.

The compound is tested for competitive inhibition at melanocortin receptors, Ki (nM) at melanocortin receptors, functional status at melanocortin receptors, ability to induce penile erection and food intake and body weight change, as in Examples 1 to 5.

EXAMPLE 8

The following compound of formula V:

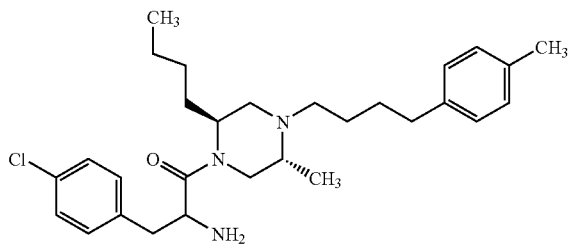

is synthesized by conventional methods. Briefly, in synthesis the following steps are employed, as set forth in Scheme 3:

To a solution of Fmoc-Norleucine alcohol A in DCM is added 1,1,1-triacetoxy-1,1-dihydro-1,2-benziodoxol-3(1H)-one (1.1 equivalent) in portions. After stirring for 30 minutes at room temperature, the solution is diluted by ether, followed by addition of 25% sodium thiosulphate in an aqueous solution saturated with sodium bicarbonate. The mixture is stirred for an additional 5 minutes and the desired compound extracted by EtOAc. The organic layer is washed by saturated bicarbonate solution, water and subsequently dried over magnesium sulfate. After evaporation of solvent, compound B is obtained for the next step reaction without further purification.

A mixture of compound B, R- or S-amino acid methyl ester (1 equivalent), or another selected amino acid methyl ester, such as an alpha amino acid with its side chain appearing as R₅ in the final compound F, TEA (1 equivalent) in the presence of a 4 Å molecular sieve in dry THF is stirred for two hours. After addition of sodium triacetoxyborohydride (1.5 equivalent) the mixture is stirred for an additional 16 hours. The solid is removed by filtration and the product extracted by EtOAc from water. The organic layer is dried over sodium sulfate. After evaporation of solvent the residue is dissolved in EtOAc containing 20% diethylamine. The reaction is carried out for 16 hours and solvent removed under vacuum. The product C is obtained after purification by chromatography.

Scheme 3

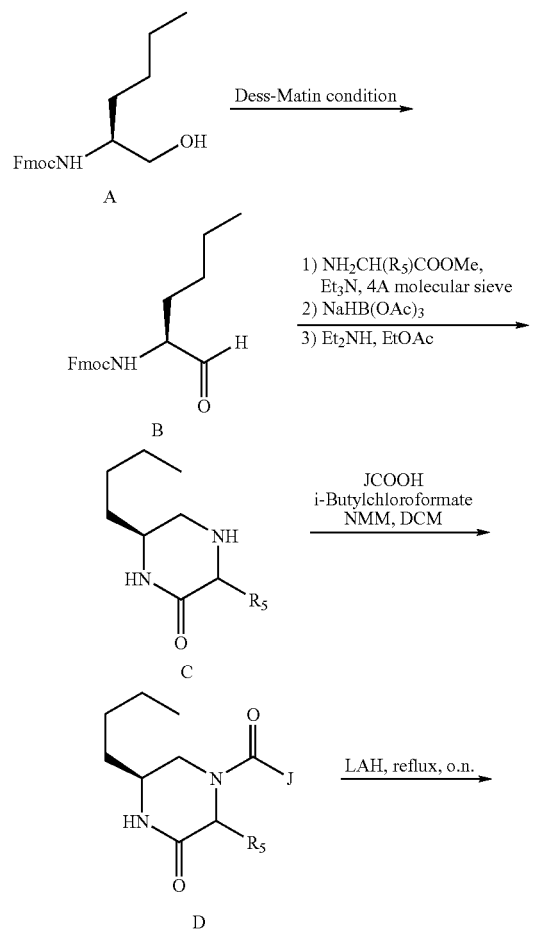

-continued

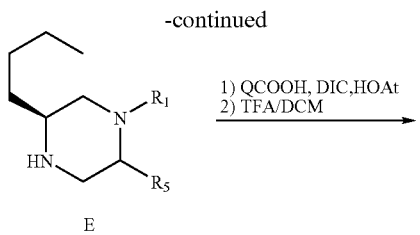

1) QCOOH, DIC, HOAt
2) TFA/DCM

E

F

To a solution of desired carboxylic acid (1 equivalent), or a related acid constituting itself as $R_1$ in the final compound F, and N-methylmorpholine (1 equivalent) in DCM at −15° C. is added isopropyl chloroformate (1 equivalent) slowly. The reaction mixture is stirred for 30 minutes and compound C is subsequently added. After 30 minutes the reaction temperature is raised to room temperature and the mixture stirred for 16 hours. The solvent is evaporated and the residue purified on column to give compound D.

To a solution of compound D in THF is added LAH (in THF, 4.5 equivalent) slowly. The reaction is conducted at room temperature for 2 hours and refluxing temperature for 16 hours. After cooling, the reaction mixture is treated with water, 15% sodium hydroxide and subsequently water. The white solids are removed by filtration and solvent is evaporated. The residue contains compound E, which is used for the next step reaction without further purification.

Compound E is coupled with desired amino acids (2 equivalent) by use of HOAt (2 equivalent) and DIC (2 equivalent) in N,N-dimethylformamide solution overnight at room temperature to introduce the desired $R_3$ moiety in the molecule. Flash chromatography gives the product with protecting groups. Fmoc groups are removed by treatment with 20% diethyl amine in EtOAc and Boc groups are removed by treatment with 30% of TFA in methylene chloride for 1 hour, as applicable to the specific compounds.

The final pure compound F is obtained by purification on HPLC.

To make the compound of Example 8, Compound E is coupled with Boc-Phe(4-Cl) as described and the Boc group is removed by treatment with 30% TFA in methylene chloride for 1 hour as described.

The compound is tested for competitive inhibition at melanocortin receptors, Ki (nM) at melanocortin receptors, functional status at melanocortin receptors, ability to induce penile erection and food intake and body weight change, as in Examples 1 to 5.

EXAMPLE 9

The following compound of formula III wherein X is $CH_2$:

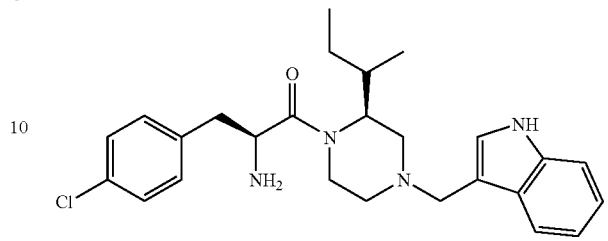

is synthesized by conventional methods. Briefly, in synthesis the following steps are employed, as set forth in Scheme 4:

Compound A (1 equivalent), N-methyl morpholine (1 equivalent) in dry DCM, is added to TBTU (1 equivalent). The mixture is stirred at room temperature for 30 minutes. A mixture of N,O-dimethylhydroxyamine hydrochloride (1.5 equivalent) and NMM (1.5 equivalent) in DCM is stirred for 30 minutes These two mixtures are combined and stirred at room temperature for 18 hours. The organic solvent is evaporated, the residue loaded on a flash chromatography column and eluted with ethyl acetae/hexane (2/1) to give an N,O-dimethylhydroxyamide product. This product is dissolved in dry THF at 0° C. and LAH (1 M in THF, 1.2 equivalent) is added slowly. After 30 minutes the reaction is quenched by aqueous potassium hydrogen sulfate (1.2 equivalent). THF is removed and ether added. The solution is washed by 1 N HCl (2 times), aqueous sodium hydrogen carbonate, and brine subsequently, and dried over sodium sulfate. The solvent is removed under vacuum to give compound B. Compound B is used for next step reaction without further purification.

Compound B is mixed with sodium triacetoxyborohydride (1.2 equivalent) and ethanolamine (1.2 equivalent) in the presence of activated 4 Å molecular sieves (1 gram) in dry THF. The mixture is stirred at room temperature for 6 hours and to it is added N-(benzyloxycarbonyloxy)succinimide (2 equivalent). It is stirred for an additional 24 hours. After filtration and evaporation of solvent the desired product C is purified on silica gel column.

Compound C is treated with 20% diethylamine in EtOAc for 12 hours and the solvent evaporated to dryness. The residue and TPP (3 equivalent) is dissolved in dry THF. To this solution is added DIAD (3 equivalent) in THF slowly at 0° C. The reaction is carried out for 16 hours at room temperature. The product D is purified on silica gel column after evaporation of solvent.

Compound D is coupled with desired amino acids (2 equivalent) by use of HOAt (2 equivalent) and DIC (2 equivalent) in N,N-dimethylformamide solution overnight at room temperature. Flash chromatography (EtOAc/hexane=2) gives the product with protecting groups E. To make the compound of Example 9, Compound D is coupled with Boc-L-Phe(4-Cl) as described to give compound E.

Compound E is treated by hydrogen in the presence of catalytic amount of palladium on carbon overnight in methanol. After filtration and removal of solvent the residue is used for reductive amination reaction with Indole-3-carboxyaldehye under the conditions described in the synthesis of compound C. The resulting compound is purified by silica gel column.

The Fmoc group is removed by treatment with 20% diethyl amine in EtOAc and the Boc group, such as on Boc-L-Phe(4-

Cl), is removed by treatment 30% TFA in methylene chloride for 1 hour, as applicable to the compounds. The final pure compounds F are obtained by purification on HPLC.

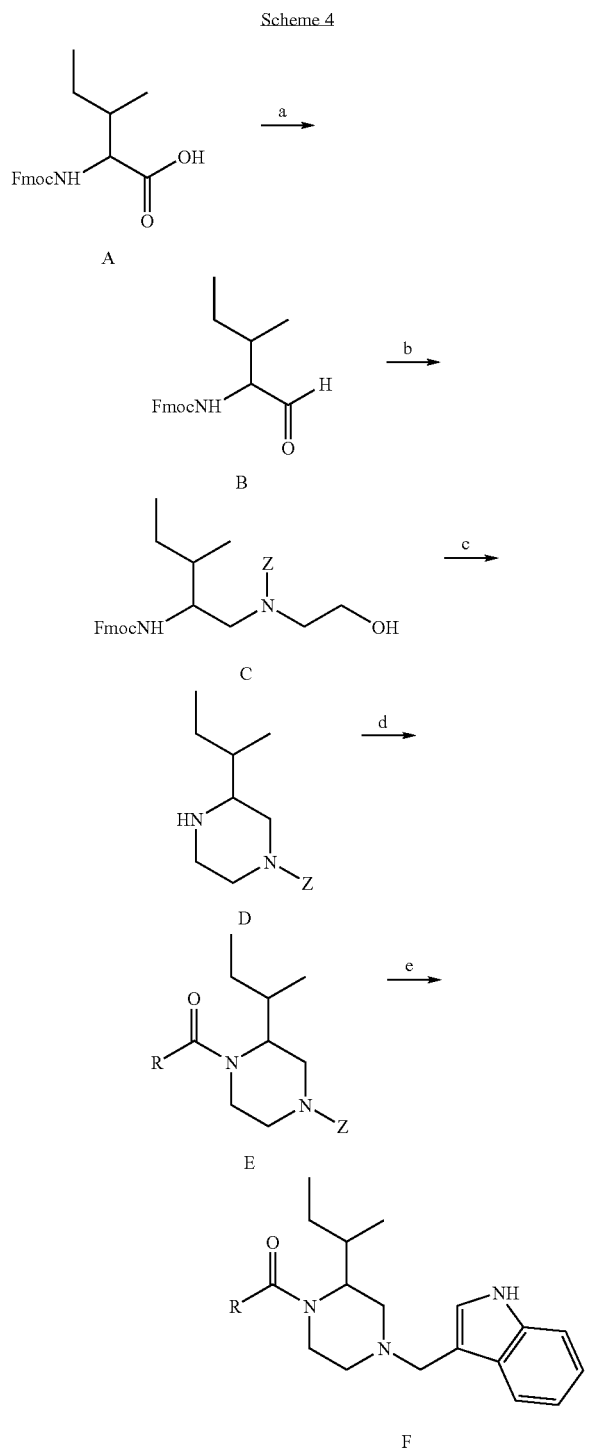

Reagents: (a) i) NHMeOMe.HCl, TBTU, NMM; ii) LAH, THF; (b) i) 4A molecular sieves, Na(AcO)₃BH, NH₂(CH₂)₂OH, THF; ii) Z—OSu; (c) i) 20% Et₂NH/EtOAc; ii) Ph3P, DIAD, THF; (d) RCOOH, HOAt, DIC, DMF; (e) i) Pd/C, Hydrogen; ii) Indole-3-carboxyaldehyde, 4A molecular sieves, NaHB(AcO)₃; iii) TFA/DCM The compound is tested for competitive inhibition at melanocortin receptors, Ki (nM) at melanocortin receptors, functional status at melanocortin receptors, ability to induce penile erection and food intake and body weight change, as in Examples 1 to 5.

EXAMPLE 10

The following compound of formula II wherein $R_2$ is H and X is C=O:

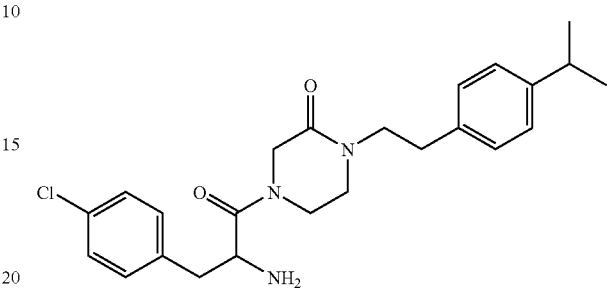

is synthesized by conventional methods. Briefly, in synthesis the following steps are employed, as set forth in Scheme 5:

To a solution of compound A and HOAt (1 equivalent) in dry N,N-dimethylformamide is added 1-(3-dimethylamino-propyl)-3-ethylcarbodimide hydrochloride (2 equivalent). After the mixture is stirred at room temperature for half an hour, ethanolamine (2 equivalent) is added. The reaction is continued for 16 hours. The reaction mixture is poured into water and extracted by EtOAc twice. The organic layer is washed by 1 N hydrochloric acid twice, 1 N sodium hydroxide twice, brine and dried over sodium sulfate. After evaporating the solvent the product B is purified on silica gel column with 10% methanol on methylene chloride.

To compound B (1 equivalent) and sodium borohydride (5 equivalent) in dioxane is added AcOH (5 equivalent) in dioxane slowly. After completion the mixture is refluxed for 2 hours. The reaction is quenched by water. The product is extracted from ether by 1 N hydrochloric acid. The pH value of the aqueous solution is adjusted with potassium hydroxide to around 11 and the product extracted by ether three times. The organic layer is dried over sodium sulfate and solvent evaporated. The obtained compound C is used for next step reaction without further purification.

A desired N-protected amino acid (1 equivalent), HOAt (1 equivalent) and DIC (1 equivalent) in N,N-dimethylformamide solution is stirred for half an hour. To this solution is added compound C and the mixture stirred overnight. After evaporating solvent, compound D is obtained by silica gel column purification.

The protecting group P (Fluorenylmethoxycarbonyl or Cbz) is removed by either 20% diethyl amine in EtOAc or by hydrogen catalyzed with 10% palladium on carbon. The resulting compound is dissolved in dry THF with TPP (3 equivalent). To this solution is added DEAD (3 equivalent) in THF slowly. The reaction is stirred for an additional 12 hours. After the solvent is evaporated the product E is purified on silica gel column by EtOAc/methanol (4/1=v/v).

Compound E is coupled with desired amino acids (2 equivalent) by use of HOAt (2 equivalent) and DIC (2 equivalent) in N,N-dimethylformamide solution overnight at room temperature. Flash chromatography (EtOAc/hexane=2) gives the product with protecting groups. The Fmoc group is removed by treatment with 20% diethyl amine in EtOAc and the Boc group is removed by treatment with 30% TFA in methylene chloride for 1 hour, as applicable to the compound. The final pure compound is obtained by purification on HPLC.

To make the compound of Example 10, Compound E is coupled with Boc-Phe(4-Cl) as described and the Boc group is removed by treatment with 30% TFA in methylene chloride for 1 hour as described.

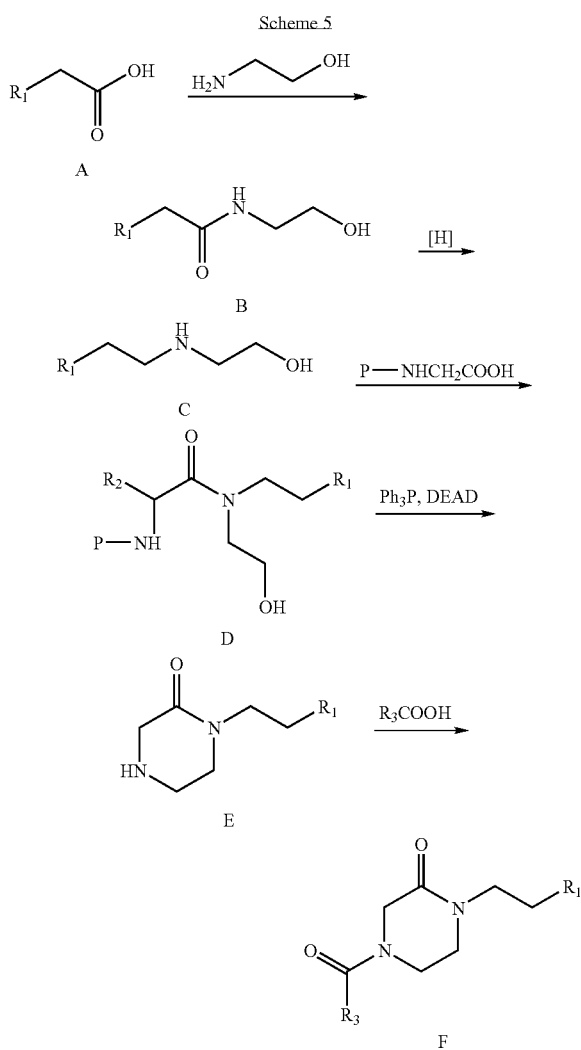

Scheme 5

The compound is tested for competitive inhibition at melanocortin receptors, Ki (nM) at melanocortin receptors, functional status at melanocortin receptors, ability to induce penile erection and food intake and body weight change, as in Examples 1 to 5.

EXAMPLE 11

The following compound of formula IX:

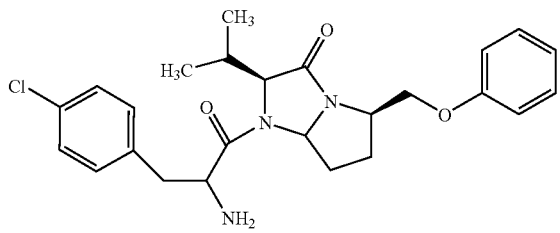

is synthesized by conventional methods. Briefly, in synthesis the following steps are employed, as set forth in Scheme 6:

To N-(tert-butoxycarbonyl)-glutamine benzyl ester and N-methyl morpholine (1 equivalent) in dry DCM is added TBTU (1 equivalent). The mixture is stirred at room temperature for 30 minutes. A mixture of N,O-dimethylhydroxyamine hydrochloride (1.5 equivalent) and NMM (1.5 equivalent) in DCM is stirred for 30 minutes. These two mixtures are combined and stirred at room temperature for 18 hours. The organic solvent is evaporated and the residue loaded on a flash chromatography column and eluted with EtOAc/hexane (2/1) to give N-(tert-butoxycarbonyl)-5-(N,O-dimethyl-hydroxamide)-glutamine benzyl ester.

N-(tert-butoxycarbonyl)-5-(N,O-dimethyl-hydroxyamide)-glutamine benzyl ester in methanol and a catalytic amount of palladium on carbon (10%) is stirred under 1 atmosphere hydrogen overnight at room temperature. After filtration and evaporation of solvent, a clear oily product is obtained.

To N-(tert-butoxycarbonyl)-5-(N,O-dimethyl-hydroxamide)-glutamine (3.9 g, 13.45 mM) and NMM (1 equivalent) in THF at −15° C. is added slowly a THF solution of IBCF (1 equivalent). The mixture is stirred at this temperature for additional 30 minutes. A solution of sodium borohydride (1.5 equivalent) in water is added in portions to the THF solution. After 20 minutes, the temperature is raised to room temperature and stirred for another 1 hour. The organic solvent is evaporated and the residue purified on column (10% methanol in DCM) to give N-(tert-butoxycarbonyl)-5-(N,O-dimethyl-hydroxamide)-glutaminol.

To N-(tert-butoxycarbonyl)-5-(N,O-dimethyl-hydroxamide)-glutaminol and TEA (2 equivalent) in DCM at 0° C. is added methanesulfonyl chloride (2 equivalent) in DCM. The solution is stirred at 0° C. for 20 minutes and at room temperature for additional 45 minutes. The solvent is evaporated and the product extracted from water by EtOAc. The organic layer is washed by water and brine and dried over sodium sulfate. After removing solvent, the yield of mesylated product is about 100%.

Sodium hydride (1.5 equivalent) is washed by hexane. After decanted hexane, dry DMF is added and the desired alcohol (1.5 equivalent) in DMF is added slowly at room temperature. The solution is stirred for another 1 hour until no hydrogen is released. The mesylated compound in DMF is mixed with the foregoing solution and stirred at room temperature for 24 hours. The solution is heated at 90° C. for additional 24 hours. After cooling, the solution is poured into water and extracted by EtOAc twice. The combined organic layer is washed by water and brine and dried over sodium sulfate. The organic solvent is removed and the residue eluted by EtOAc/hexane (2/1) on a column to give O-alkylated N-(tert-butoxycarbonyl)-5-(N,O-dimethyl-hydroxamide)-glutaminol, compound A in Scheme 6.

Compound A is stirred in TFA/DCM (1/4:v/v) for one hour. The solvent is removed and dried under vacuum. The residue is mixed with NMM (4 equivalent) in DCM. To a DCM solution of Z-Ala-OH (2 equivalent) and NMM (2 equivalent) is added TBTU (2 equivalent) and the mixture is stirred for 30 minutes These two solutions are combined and stirred overnight at room temperature. After evaporating solvent and purification on a column by EtOAc, O-alkylated N-(N-benzyloxy-valyl)-5-(N,O-dimethyl-hydroxamide)-glutaminol is obtained. O-alkylated N-(N-Cbz-valyl)-5-(N,O-dimethyl-hydroxamide)-glutaminol is dissolved in dry THF. The solution is cooled to 0° C. under nitrogen atmosphere. To this solution is added LAH (1 M in THF, 1.25 equivalent) slowly. The solution is stirred at this temperature for 30 minutes. The reaction is stopped by adding potassium hydrogen sulfate (1.5 equivalent) in water. After stirring for 30 minutes, the solvent is removed and re-dissolved in ether. The organic phase is washed by 1 N hydrochloric acid, saturated sodium hydrogen carbonate and brine. The ether layer is dried over sodium sulfate. Solvent is removed to give an aldehyde derivative, which is used for the next step reaction without further purification. The aldehyde derivative is dissolved in DCM containing a catalytic amount of TFA. The solution is refluxed for 5 hours.

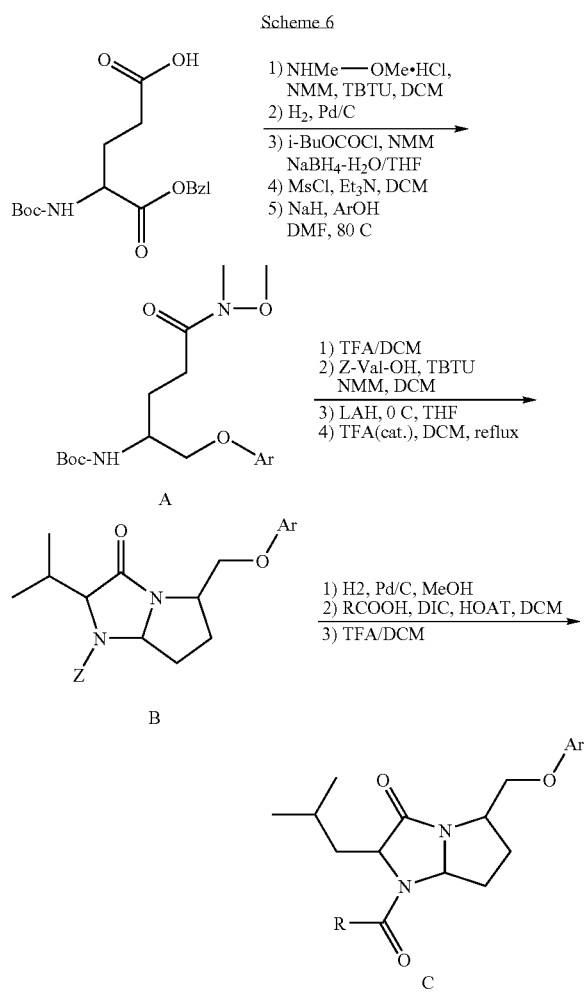

After removing solvent, the residue is purified on a column to give compound B. Compound B is dissolved in methanol in the presence of catalytic amounts of palladium on carbon (10%). The mixture is stirred under hydrogen (1 atmosphere) overnight. After filtration and evaporation of solvent, the residue is dried under vacuum to give 2,5-substituted hexahydro-pyrrolo[1,2-a]imidazol-3-one. This compound is coupled with desired amino acids (2 equivalent) by use of HOAt (2 equivalent) and DIC (2 equivalent) in N,N-dimethylformamide solution overnight at room temperature.

To make the compound of Example 11, 2,5-substituted hexahydro-pyrrolo[1,2-a]imidazol-3-one is coupled with Boc-Phe(4-Cl) as described.

Flash chromatography (EtOAc/hexane=2) gives the product with protecting groups. The Fmoc group is removed by treatment with 20% diethyl amine in EtOAc and the Boc group removed by treatment with 30% TFA in methylene chloride for 1 hour, as applicable to the compounds. The final pure compounds C are obtained by purification on HPLC.

The compound is tested for competitive inhibition at melanocortin receptors, Ki (nM) at melanocortin receptors, functional status at melanocortin receptors, ability to induce penile erection and food intake and body weight change, as in Examples 1 to 5.

EXAMPLE 12

The following compound is synthesized by conventional methods. Briefly, in synthesis the following steps are employed, as set forth in Scheme 7:

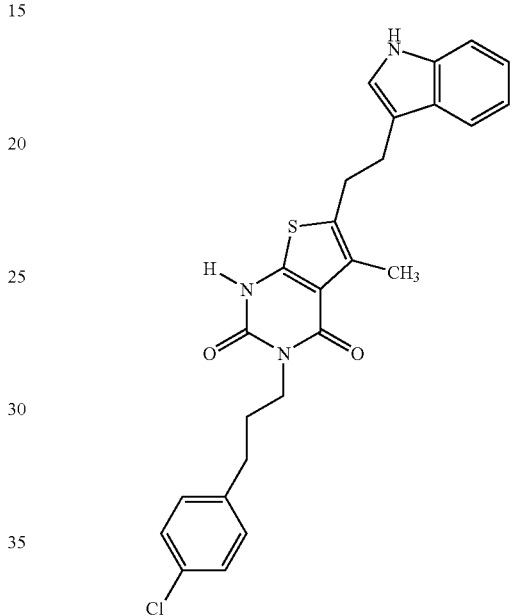

A mixture of ketone (1 equivalent), ethyl cyanoacetae (1 equivalent), ammonium acetate (0.2 equivalent) and AcOH (0.8 equivalent) is refluxed in toluene for 20 hours with a Dean-Stark apparatus. The mixture is concentrated. The residue is diluted with saturated sodium hydrogen carbonate and extracted with chloroform. The organic layer is washed with brine and dried over magnesium sulfate. After evaporation of solvent the residue is purified on silica gel column. This purified compound is dissolved in ethanol. To this solution is added sulfur powder (1 equivalent) and diethylamine (1 equivalent). The solution is stirred at 65° C. for 2 hours. The solvent is removed and the residue is diluted with brine and extracted with chloroform. The extract is washed with brine and dried over magnesium sulfate. The solution is concentrated and residue purified on silica gel column or recrystallized from a suitable solvent to give compound A.

To make the compound of Example 12, 1-(1H-Indol-3-yl)-pentan-3-one is used as the starting material to form compound A. 3-iodo-1-(4-chlorophenyl)propane is used to make compound C from compounds B as described.

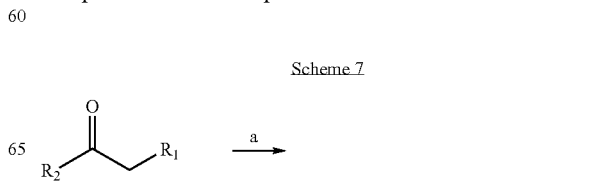

-continued

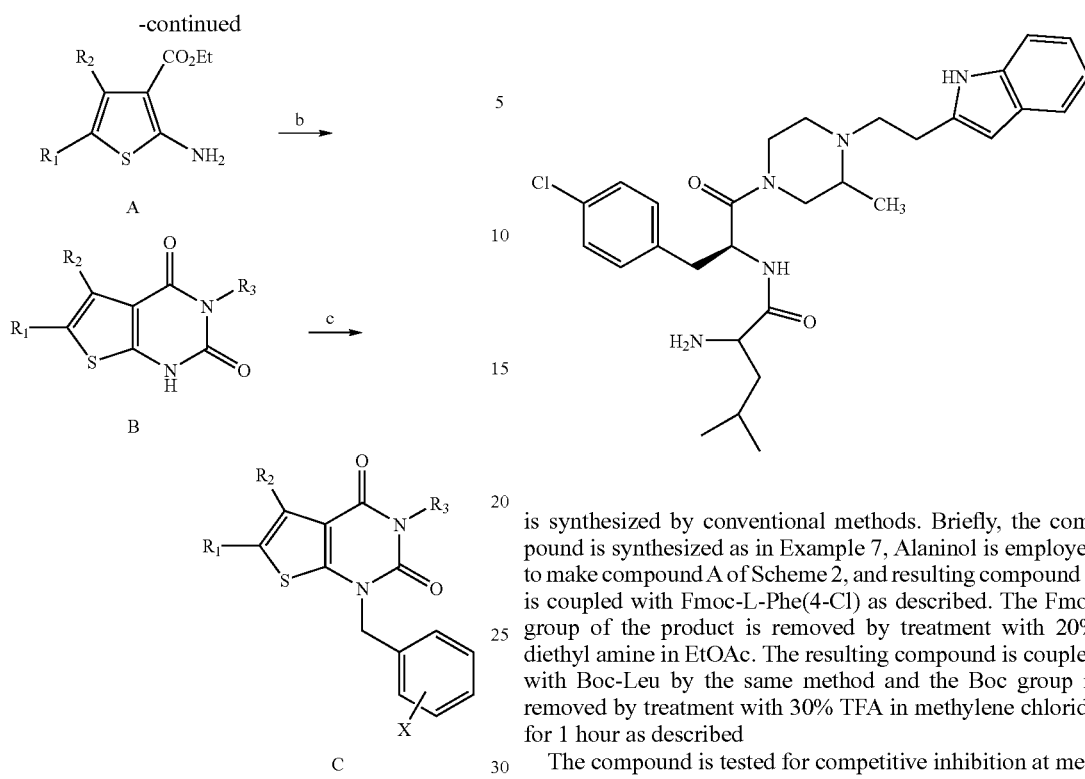

Reagents: (a) i) ethyl cyanoacetate, AcNH$_4$, AcOH, toluene, ii) sulfur powder, Et$_2$NH,EtOH; (b) i) R$_3$NCO, pyridine, ii) NaOMe, MeOH; (c) X-substituted benzylchloride, K$_2$CO$_3$, KI, DMF.

A mixture of compound A and a desired isocyanate (1.2 equivalent) in pyridine is stirred at 45° C. for 2 hours. After removal of solvent the residue is suspended in methanol and sodium methoxide (2.5 equivalent) is added. The mixture is stirred at room temperature for 6 hours and acidified with 2 N hydrochloric acid at 0° C. The solvent is removed and the precipitates (B) are collected. After washing with water compound B is dried under vacuum.

A mixture of compound B, substituted benzyl chloride (1.2 equivalent), potassium carbonate (1.5 equivalent) and potassium iodide (0.5 equivalent) in DMF is stirred at room temperature for 4 hours. The solvent is removed and the residue is partitioned between chloroform and water. The aqueous phase is extracted with chloroform. The combined organic phase is washed with brine and dried over magnesium sulfate. After removal of solvent the residue is recrystallized from a suitable solvent to give compound C.

The compound is tested for competitive inhibition at melanocortin receptors, Ki (nM) at melanocortin receptors, functional status at melanocortin receptors, ability to induce penile erection and food intake and body weight change, as in Examples 1 to 5.

EXAMPLE 13

The following compound of formula VI wherein R$_2$ and R$_5$ are H, and R$_4$ is —CH$_3$:

is synthesized by conventional methods. Briefly, the compound is synthesized as in Example 7, Alaninol is employed to make compound A of Scheme 2, and resulting compound E is coupled with Fmoc-L-Phe(4-Cl) as described. The Fmoc group of the product is removed by treatment with 20% diethyl amine in EtOAc. The resulting compound is coupled with Boc-Leu by the same method and the Boc group is removed by treatment with 30% TFA in methylene chloride for 1 hour as described The compound is tested for competitive inhibition at melanocortin receptors, Ki (nM) at melanocortin receptors, functional status at melanocortin receptors, ability to induce penile erection and food intake and body weight change, as in Examples 1 to 5.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A compound of the general formula VIII or IX:

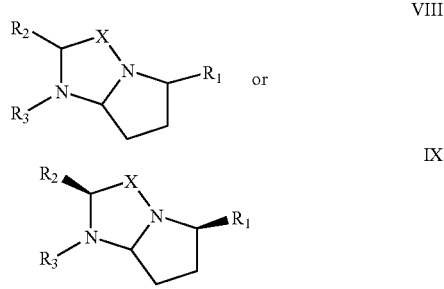

wherein:

R$_1$ is a bond or a linker unit with from one to six atoms joined one to the other by bonds and forming a chain selected from the group consisting of carbon (C), oxygen (O) and nitrogen (N) and a ring group including at least one substituted or unsubstituted aromatic ring, including carbocyclic or heterocyclic aromatic rings, bicylic ring groups, and bridged ring groups wherein at least one ring is an aromatic ring, and fused ring groups other than 6,6-membered fused ring structures wherein at least one ring is an aromatic ring;

$R_2$ is hydrogen (H) or a $C_1$ to $C_6$ aliphatic linear or branched chain;

$R_3$ is a natural or unnatural L- or D-amino acid with a carbocyclic aromatic group-containing side chain, a natural or unnatural L- or D-amino acid with a carbocyclic aromatic group-containing side chain and an amine capping group, or is -$R_6$-$R_7$;

$R_6$ is a D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-Me), Phe(4-OMe), Phe(4-NC), or Phe(4-NO$_2$);

$R_7$ is -$R_8$, -$R_9$ or -$R_8$-$R_9$;

$R_8$ is between one and three natural or unnatural L- or D-amino acids;

$R_9$ is an amine capping group;

X is (CH$_2$)$_n$, CH, NH, N, O, C=O, C=S, S, S=O or SO$_2$; and n is 0, 1, 2 or 3.

2. The compound of claim 1, wherein $R_1$ is:

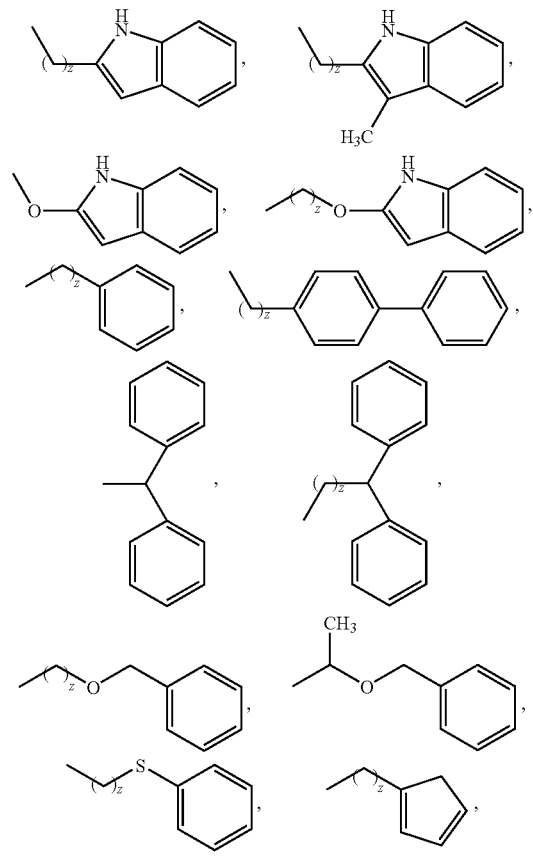

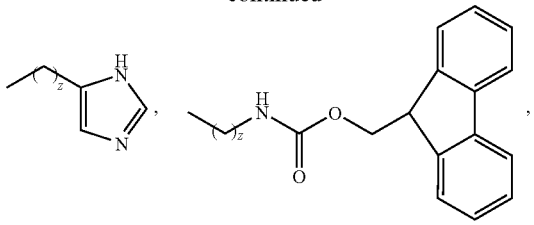

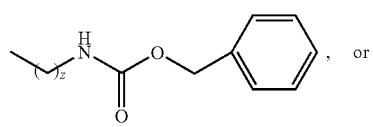

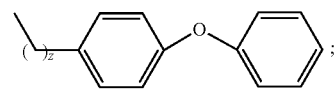

where z is from 1 to 5.

3. The compound of claim 2, wherein at least one aromatic ring of $R_1$ has one or more halogen, alkyl or aryl substituents.

4. The compound of claim 1, wherein $R_2$ is —CH$_3$, —(CH$_2$)$_y$CH$_3$, where y is from 1 to 5, or is

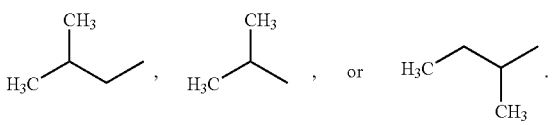

5. The compound of claim 1 wherein $R_3$ is a D-amino acid.

6. The compound of claim 5 wherein $R_3$ is a D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-Me), Phe(4-OMe), Phe(4-NC), or Phe(4-NO$_2$).

7. The compound of claim 1 wherein the amine capping group is selected from the group consisting of methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc and 8-Aoc.

8. The compound of claim 1, wherein the carbocyclic aromatic group of the carbocyclic aromatic group-containing side chain of $R_3$ is:

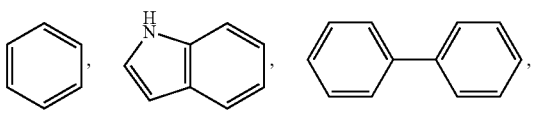

-continued
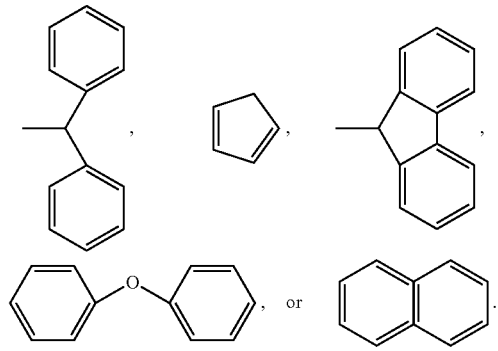
9. The compound of claim 1, wherein the carbocyclic aromatic group of the carbocyclic aromatic group-containing side chain of $R_3$ is:
-continued
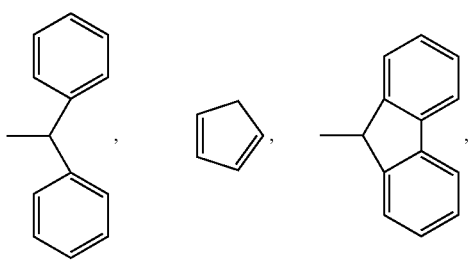
with one or more halogen, alkyl or aryl substituents.
* * * * *